(12) United States Patent
Cerrina et al.

(10) Patent No.: US 7,037,659 B2
(45) Date of Patent: May 2, 2006

(54) APPARATUS FOR CONSTRUCTING DNA PROBES HAVING A PRISMATIC AND KALEIDOSCOPIC LIGHT HOMOGENIZER

(75) Inventors: Francesco Cerrina, Madison, WI (US); Wei Huang, Madison, WI (US)

(73) Assignee: Nimblegen Systems Inc., Madison, WI (US)

( * ) Notice: Subject to any disclaimer, the term of this patent is extended or adjusted under 35 U.S.C. 154(b) by 601 days.

(21) Appl. No.: 10/277,530

(22) Filed: Oct. 21, 2002

(65) Prior Publication Data

US 2003/0143132 A1   Jul. 31, 2003

Related U.S. Application Data

(60) Provisional application No. 60/353,491, filed on Jan. 31, 2002.

(51) Int. Cl.
*C12Q 1/68* (2006.01)
*C12M 1/00* (2006.01)
*C12M 1/36* (2006.01)
*B01J 19/00* (2006.01)
*C07H 21/00* (2006.01)

(52) U.S. Cl. .................... 435/6; 435/283.1; 435/287.2; 422/68.1; 422/131; 536/25.3

(58) Field of Classification Search .................... 435/6, 435/283.1, 287.2; 422/68.1
See application file for complete search history.

(56) References Cited

U.S. PATENT DOCUMENTS

| | | | | |
|---|---|---|---|---|
| 4,561,748 | A | * | 12/1985 | Omaki et al. ................ 396/110 |
| 6,259,512 | B1 | * | 7/2001 | Mizouchi ...................... 355/67 |
| 6,271,957 | B1 | * | 8/2001 | Quate et al. ................. 359/298 |
| 6,295,153 | B1 | | 9/2001 | Garner |
| 6,375,903 | B1 | * | 4/2002 | Cerrina et al. .............. 422/131 |
| 6,426,184 | B1 | * | 7/2002 | Gao et al. ...................... 435/6 |

* cited by examiner

*Primary Examiner*—BJ Forman
(74) *Attorney, Agent, or Firm*—Quarles & Brady LLP

(57) ABSTRACT

The present invention provides an apparatus for constructing arrays of DNA sequences using the image of a micromirror array projected on a reaction site using a highly uniform beam of light produced by a homogenizer formed of a prismatic refractive element followed by a kaleidoscopic element.

10 Claims, 18 Drawing Sheets

APPARATUS FOR CONSTRUCTING DNA PROBES HAVING A PRISMATIC AND KALEIDOSCOPIC LIGHT HOMOGENIZER

CROSS REFERENCE TO RELATED APPLICATION

This application is based on provisional application 60/353,491 filed Jan. 31, 2002 and entitled "Method and Apparatus for Synthesis of DNA Probes" and claims the benefit thereof.

FIELD OF THE INVENTION

This invention pertains generally to the field of biology and particularly to techniques and apparatus for the manufacture of arrays of polymers useful in the analysis and sequencing of DNA and related polymers.

BACKGROUND OF THE INVENTION

The sequencing of deoxyribonucleic acid (DNA) is a fundamental tool of modern biology and is conventionally carried out in various ways, commonly by processes which separate DNA segments by electrophoresis. See, e.g., "DNA Sequencing," *Current Protocols In Molecular Biology*, Vol. 1, Chapter 7 (1995).

The sequencing of several important genomes has already been completed (e.g., yeast, *E. coli*, human, *C. elegans*, *Arabidopsis*), and work is proceeding on the sequencing of other genomes of medical and agricultural importance. In the medical context, it will be necessary to "re-sequence" the genome of large numbers of human individuals to determine which genotypes are associated with which diseases. Such sequencing techniques can be used to determine which genes are active and which are inactive, either in specific tissues, such as cancers, or more generally in individuals exhibiting genetically influenced diseases. The results of such investigations can allow identification of the proteins that are good targets for new drugs or identification of appropriate genetic alterations that may be effective in genetic therapy. Other applications lie in fields such as soil ecology or pathology where it would be desirable to be able to isolate DNA from any soil or tissue sample and use probes from ribosomal DNA sequences from all known microbes to identify the microbes present in the sample.

The conventional sequencing of DNA using electrophoresis is typically laborious and time consuming. Various alternatives to conventional DNA sequencing have been proposed. One such alternative approach, utilizing an array of oligonucleotide probes synthesized by photolithographic techniques is described in Pease, et al., "Light-Generated Oligonucleotide Arrays for Rapid DNA Sequence Analysis," *Proc. Natl. Acad. Sci. USA*, 91: 5022–5026 (May 1994). In this approach, the surface of a solid support modified with photolabile protecting groups is illuminated through a photolithographic mask, yielding reactive hydroxyl groups in the illuminated regions. A 3' activated deoxynucleoside, protected at the 5' hydroxyl with a photolabile group, is then provided to the surface such that coupling occurs at sites that had been exposed to light. Following capping, and oxidation, the substrate is rinsed and the surface is illuminated through a second mask to expose additional hydroxyl groups for coupling. A second 5' protected activated deoxynucleoside base is presented to the surface. The selective photo-deprotection and coupling cycles are repeated to build up levels of bases until the desired set of probes is obtained.

It may be possible to generate high density miniaturized arrays of oligonucleotide probes using such photolithographic techniques wherein the sequence of the oligonucleotide probe at each site in the array is known. These probes can then be used to search for complementary sequences on a target strand of DNA, with detection of the target that has hybridized to particular probes accomplished by the use of fluorescent markers coupled to the targets and inspection by an appropriate fluorescence scanning microscope. A variation of this process using polymeric semiconductor photoresists, which are selectively patterned by photolithographic techniques, rather than using photolabile 5' protecting groups, is described in McGall, et al., "Light-Directed Synthesis of High-Density Oligonucleotide Arrays Using Semiconductor Photoresists," *Proc. Natl. Acad. Sci. USA*, 93:13555–13560 (November 1996), and G. H. McGall, et al., "The Efficiency of Light-Directed Synthesis of DNA Arrays on Glass Substrates," *Journal of the American Chemical Society* 119:22:5081–5090 (1997).

A disadvantage of both of these approaches is that four different lithographic masks are needed for each monomeric base, and the total number of different masks required are thus four times the length of the DNA probe sequences to be synthesized. The high cost of producing the many precision photolithographic masks that are required, and the multiple processing steps required for repositioning of the masks for every exposure, contribute to relatively high costs and lengthy development times.

The parent application to the present application describes a method and apparatus for the synthesis of arrays of DNA probe sequences, polypeptides, and the like without photolithographic masks by using a dynamic mask image produced by an array of switchable optical elements, such as a two-dimensional array of electronically addressable micromirrors. Each of the micromirrors can be selectively switched between one of at least two separate positions so as to contribute light to the mask image in a first position, and to deflect the light to an absorber in a second position. Projection optics receive the light reflected from the mirror array and produce an image of the mirrors onto a flow cell or substrate where the nucleotide addition reactions are conducted.

In order that the nucleotide addition reactions be properly controlled, it is desirable that the light intensity at each mirror be relatively constant over the entire mirror array ensuring similar reactions of nucleotides at mirror images on the substrate.

The source of the light is normally an electrical arc that provides both high intensity and suitable spectral components for the nucleotide reactions. A collimator lens system is used to convert the point source of the arc to a more uniform field. Normally, however, the collimated light will exhibit a spatially low order variation, for example, a general falling off of light intensity at the field edges that is very undesirable. A uniformity of better than 5% is usually required.

One method of improving the uniformity of the collimated light is through the use of a "diffuser screen" or "diffusion lens" introducing scatter into the light field. Diffusion systems suitable for correcting substantial low order intensity variations, however, may result in undesirable light losses.

SUMMARY OF THE INVENTION

The present invention provides a highly uniform light field using a combination of a refractive prism followed by an internally reflecting kaleidoscope element. The prism breaks up the light field in a number of virtual sources which is then further broken by the kaleidoscope element to yield a globally uniform field.

Specifically, the present invention provides an apparatus for constructing DNA probes, and the like, having a reactor providing a reaction site at which nucleotide addition reactions may be conducted and a light source providing light capable of promoting nucleotide addition reactions. A set of electronically addressable micromirrors is positioned along an optical path between the light source and the reactor to receive and reflect the light and a prismatic/kaleidoscopic light homogenizer is positioned on the optical path between the light source and the electronically addressable micromirror. The prismatic/kaleidoscopic light homogenizer includes a light transmitting refractive prism followed by an internally reflecting kaleidoscopic element positioned to receive light refracted by the refractive prism.

Thus it is one object of the invention to provide for a robust and predictable light homogenizer having low absorption.

It is another object of the invention to provide for such a system having a shorter length than normal kaleidoscopic elements Further objects, features and advantages of the invention will be apparent from the following detailed description when taken in conjunction with the accompanying drawings.

DETAILED DESCRIPTION OF THE INVENTION

In the prior art, the manufacture of DNA arrays required the production of a series of photographic masks for the synthesis of each nucleotide position for the nucleotides in the array. Here it is taught that the use of the photographic masks can be entirely avoided. It is now possible, and quite practical, to substitute an array of optical switches for the masks with such arrays containing large numbers of optical switching elements that are individually addressable and operable under software control. The use of such optical arrays permits the entire DNA array synthesis process to be completely flexible and permits the convenient and rapid manufacture of custom arrays in a manner not previously provided.

Also in the prior art, the manufacture of DNA arrays required that the synthesis of each nucleotide sequence occur on the substrate intended to serve as the array. Here it is taught that the synthesis of the nucleotide sequences may be performed in a solution phase, free from the substrate intended to serve as the array, as well as directly on the substrate. The synthesis of the nucleotide sequences in a solution phase provides several distinct advantages over the prior art. First, it allows for the synthesis of longer probes and the removal of any non-homogenous probes resulting from failed chemical reactions, which can account for greater than fifty percent of the probe population. It also allows for quality control as eluate from select channels may be collected and analyzed to verify the content of the microarray, thus providing a means for testing the microarray to satisfy the rigorous standards required in clinical settings. Finally, the synthesis of nucleotide sequences in a solution phase allows for the production of biologically active microarrays. These arrays would contain probes available for primer extension reactions useful in a host of possible applications, such as the direct hybridization of mRNA followed by the extension of the probe/primer with reverse transcriptase in the presence of a label.

Figure 1:
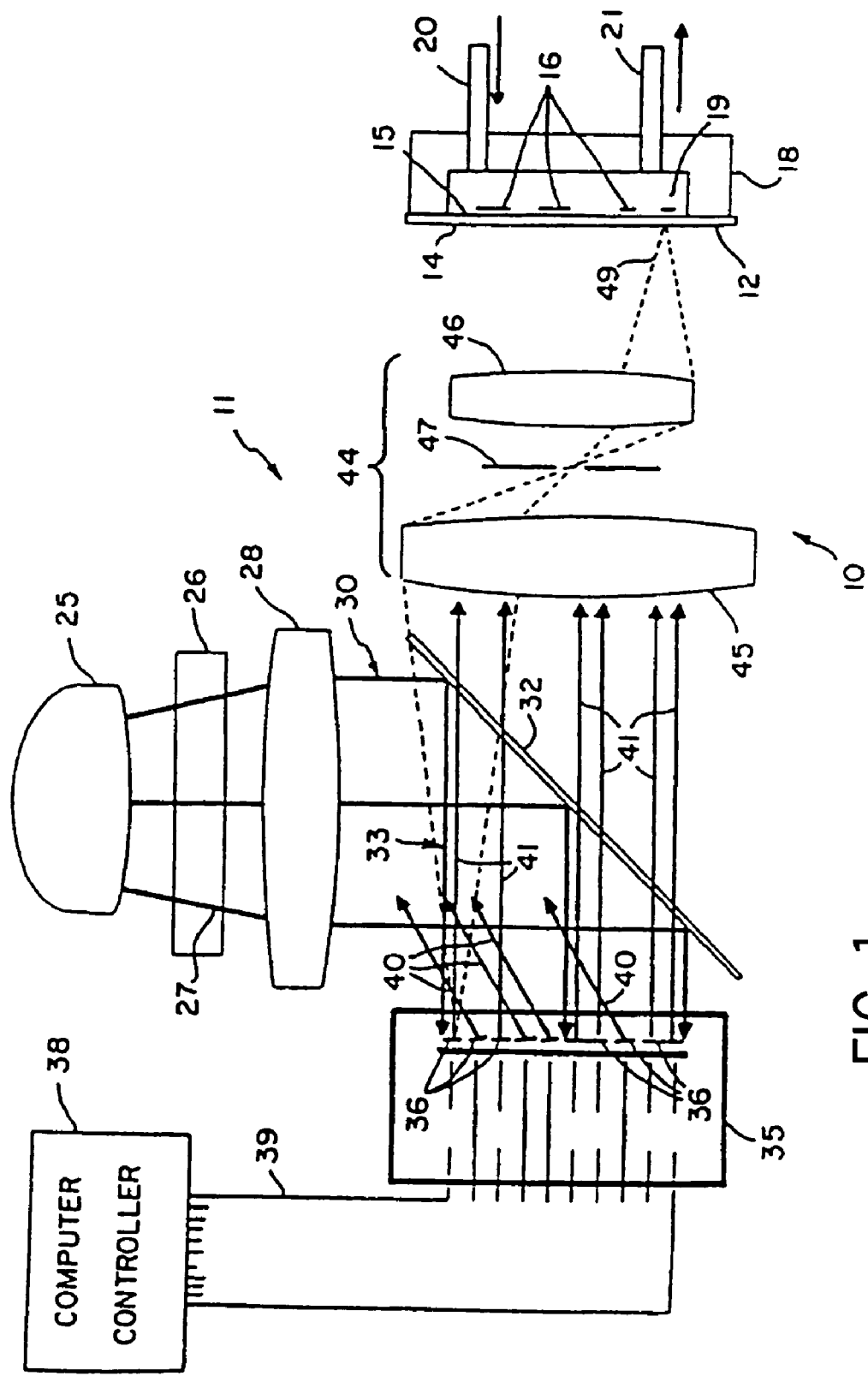
FIG. 1 is a schematic view of an array synthesizer apparatus in accordance with the present invention.

With reference to the drawings, one exemplary apparatus using a flow cell with a single reaction chamber and a micromirror light array is shown generally at 10 in FIG. 1. The apparatus includes a two-dimensional array image former 11 and a substrate 12 onto which the array image is projected by the image former 11. For the configuration shown in FIG. 1, the substrate has an exposed entrance surface 14 and an opposite active surface 15 on which a two-dimensional array of nucleotide sequence probes 16 are to be fabricated. The substrate 12 is mounted in a flow cell reaction chamber 18 enclosing a volume 19 into which reagents can be provided through an input port 20 and an output port 21. However, the substrate 12 may be utilized in the present system with the active surface 15 of the substrate facing the image former 11 and enclosed within a flow cell with a transparent window to allow light to be projected onto the active surface. The invention may also use an opaque or porous substrate. The reagents may be provided to the ports 20 and 21 from a conventional DNA oligonucleotide synthesizer (not shown in FIG. 1).

The image former 11 allows for the direction of light from a light source 25 along an optical light path and into the flow cell reaction chamber 18 so that nucleotide addition reactions may occur in accordance with a pre-selected pattern. The image former 11 includes the light source 25 (e.g., an ultraviolet or near ultraviolet source such as a mercury arc lamp), an optional filter 26 to receive the output beam 27 from the source 25 and selectively pass only the desired wavelengths (e.g., the 365 nm Hg line), and a condenser system 28 for forming a collimated beam 30. Other devices for filtering or monochromating the source light, e.g., diffraction gratings, dichroic mirrors, and prisms, may also be used rather than a transmission filter, and are generically referred to as "filters" herein.

Figure 21:
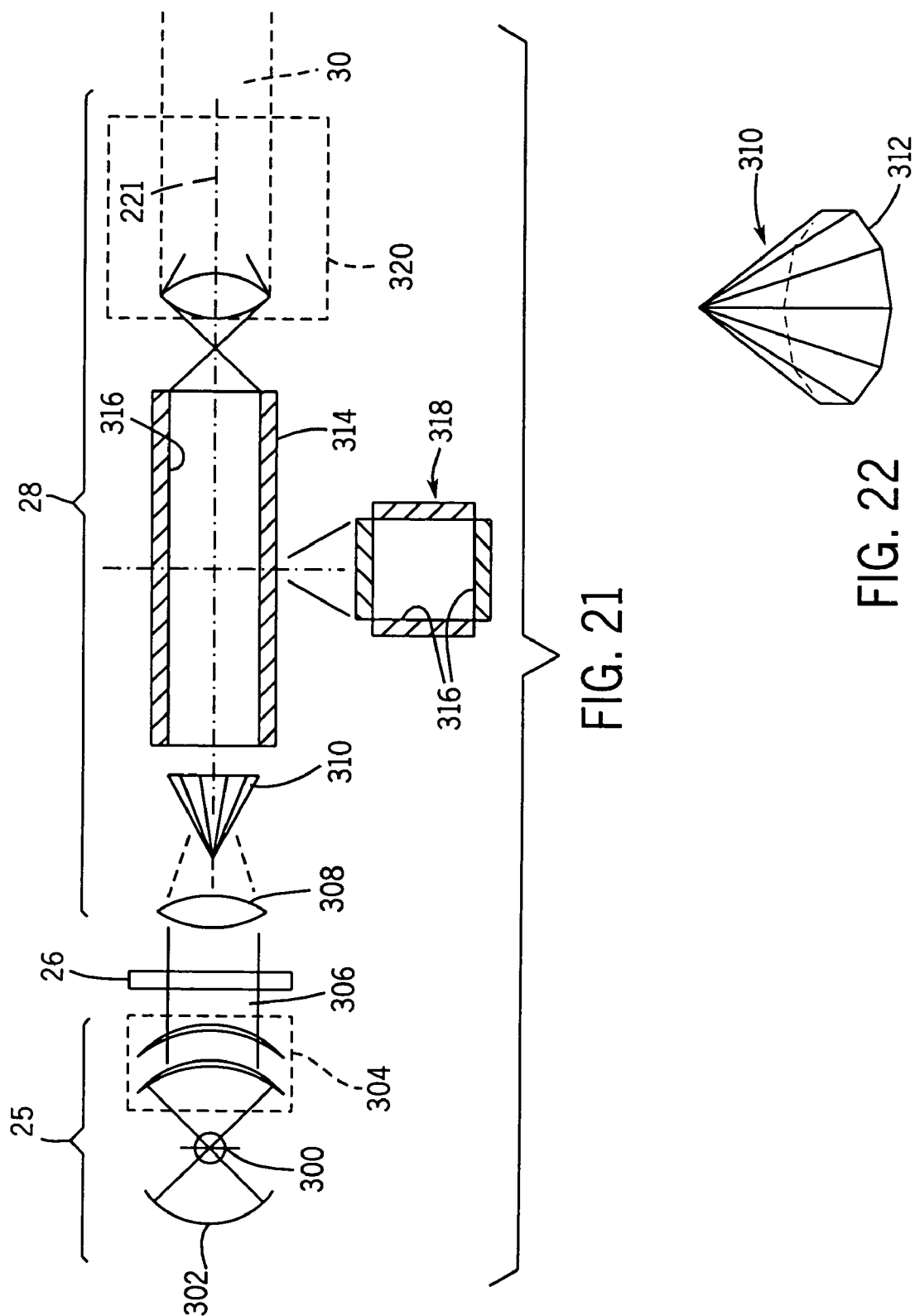
FIG. 21 is a simplified representation of an optical collimation system including the prismatic/kaleidoscopic light homogenizer of the present invention and showing an example cross section for the kaleidoscopic element.

Referring now to FIG. 21, the light source 25 may provide an electrical arc 300 producing an intense point source of light. The arc 300 may be backed by a spherical reflector 302 to project light forward along the optical path 221 toward a condenser lens system 304.

The condenser lens system 304 produces a collimated light beam 306 that may be received by optional filter 26 and then focused by lens 308 on refractive prism element 310. The term "prism" as used herein, refers to an optical prism having a polyhedral surface of flat faces or "faucets" in distinction from the smoothly varying surface of lenses.

Figure 22:
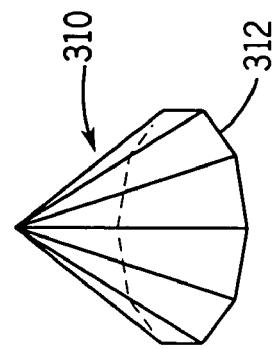
FIG. 22 is a perspective view of the prismatic element of the collimator of FIG. 21.

The prismatic element 310 may, for example, be a pyramid with an octagonal base 312 as shown in FIG. 22 and constructed of a standard optical glass. Referring again to FIG. 21, the apex of the pyramid of the prismatic element 310 is directed toward the arc 300 while the base 312 is aligned to be generally perpendicular to the optical path 221.

Light passing through the prismatic element 310 is received by a central l bore 316 of kaleidoscope element 314. The inner walls of the bore 316 are reflective either by virtue of their high index of refraction over that of air or by metallization or the like, well known in the art.

The bore 316 of the kaleidoscope element 314 may employ any of a variety of different cross sections, however, in the preferred embodiment, a square cross section 318, is used. Other cross sections such as provide for regular tiling of a plane may also be used.

Light exiting the kaleidoscopic element 314 is received by additional collimating elements 320 such as may complete a Kohler illumination system well known in the art. The resulting collimated beam 30 may then be directed toward the array of optical elements 35 such as the DLP.

An optional diffuser may also be added to the system, however, this is not necessary provided the remaining inhomogeneities in the intensity of the beam 30 have a spatial frequency significantly less than the image being produced.

In one embodiment, the beam 30 is projected onto a beam splitter 32 (pellicle or glass) which reflects a portion of the beam 30 into a beam 33 which is projected onto an array of optical elements 35. To use a light switch at normal incidence, a device that allows illumination and image formation at the same time is necessary. With devices allowing an angular deflection, this is not necessary since a side illumination can be used.

The optical array 35 is preferably a two-dimensional array of small or miniature optical elements which are operable under electronic control such that they may be operated by the output of a general purpose digital computer connected to the optical array 35. The optical array 35 must include optical elements which are capable of, in effect, switching light in amplitude, direction, or other attribute of the light, sufficient to change a portion of the incident light from one state where that portion of the light actuates a reaction occurring in one cell on the substrate 12 in the flow cell 18. There are several examples of optical devices which can serve as the optical array 35. One is an array of micromirrors, which is a preferred example as described further in much greater detail immediately below. Other types of suitable optical arrays include without limitation microshutters, micromirrors operated by bimorph piezoelectric actuators, LCD shutters, and reflective LCD devices.

Figure 2:
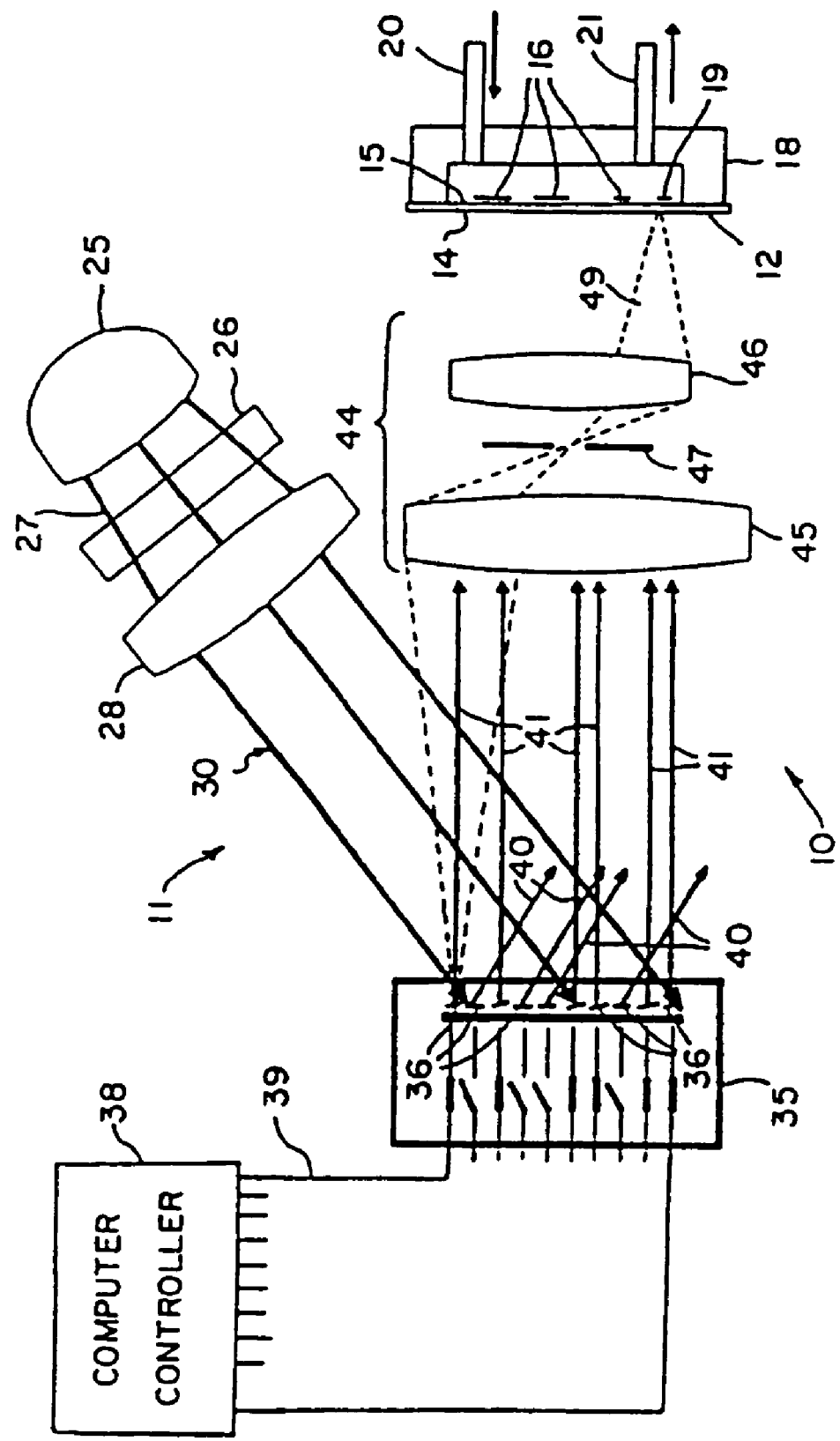
FIG. 2 is a schematic view of another array synthesizer apparatus in accordance with the present invention.

A micromirror array device employed as the optical array 35 is illustrated in FIGS. 1 and 2. The micromirror array device 35 has a two-dimensional array of individual micromirrors 36 which are each responsive to control signals supplied to the array device 35 to tilt in one of at least two directions. Control signals are provided from a computer controller 38 on control lines 39 to the micromirror array device 35. The micromirrors 36 are constructed so that in a first position of the mirrors the portion of the incoming beam of light 33 that strikes an individual micromirror 36 is deflected in a direction oblique to the incoming beam 33, as indicated by the arrows 40. In a second position of the mirrors 36, the light from the beam 33 striking such mirrors in such second position is reflected back parallel to the beam 33, as indicated by the arrows 41. The light reflected from each of the mirrors 36 constitutes an individual beam 41. Other types of suitable devices include phase controlling switches, such as variable gratings or variable height systems.

The multiple beams 41 are incident upon the beam splitter 32 and pass through the beam splitter with reduced intensity and are then incident upon projection optics 44 indicated conceptually by lenses 45 and 46 and optional adjustable iris 47, but not limited to this. The projection optics 44 serve to form an image of the pattern of the micromirror array 35, as represented by the individual beams 41 (and the dark areas between these beams), on the active surface 15 of the substrate 12. The outgoing beams 41 are directed along a main optical axis of the image former 11 that extends between the micromirror device and the substrate. The substrate 12 in the configuration shown in FIG. 1 is transparent, e.g., formed of fused silica or soda lime glass or quartz, so that the light projected thereon, illustratively represented by the lines labeled 49, passes through the substrate 12 without substantial attenuation or diffusion.

A preferred micromirror array 35 is the Digital Light Processor (DLP) available commercially from Texas Instruments, Inc. These devices have arrays of micromirrors (each of which is substantially a square with edges of 10 to 20 μm in length) which are capable of forming patterned beams of light by electronically addressing the micromirrors in the arrays. Such DLP devices are typically used for video projection and are available in various array sizes, e.g., 640×800 micromirror elements (512,000 pixels), 640×480 (VGA; 307,200 pixels), 800×600 (SVGA; 480,000 pixels); and 1024×768 (XGA 786,432 pixels). Such arrays are discussed in the following article and patents: Larry J. Hornbeck, "Digital Light Processing and MEMs: Reflecting the Digital Display Needs of the Networked Society," SPIE/EOS European Symposium on Lasers, Optics, and Vision for Productivity and Manufacturing 1, Besancon, France, Jun. 10–14, 1996; and U.S. Pat. Nos. 5,096,279, 5,535,047, 5,583,688 and 5,600,383.

The micromirrors 36 of such devices are capable of reflecting the light of normal usable wavelengths, including ultraviolet and near ultraviolet light, in an efficient manner without damage to the mirrors themselves. The window of the enclosure for the micromirror array preferably has anti-reflective coatings thereon optimized for the wavelengths of light being used. Utilizing commercially available 600×800 arrays of micromirrors, encoding 480,000 pixels, with typical micromirror device dimensions of 16 microns per mirror side and a pitch in the array of 17 microns, provides total micromirror array dimensions of 13,600 microns by 10,200 microns.

The magnification of the optics can be designed to provide any final chip or image size. For instance, by using a reduction factor of 5 through the optics system 44, a typical and readily achievable value for a lithographic lens, the dimensions of the image projected onto the substrate 12 are thus about 2,220 microns by 2,040 microns, with a resolution of about 2 microns. This resolution can be accommodated by using only every other mirror of the micromirrors 36. Larger images can be exposed on the substrate 12 by utilizing multiple side-by-side exposures (by either stepping the flow cell 18 or the image projector 11), or by using a larger micromirror array. It is also possible to do one-to-one imaging without reduction as well as enlargement of the image on the substrate, if desired.

Preferably, however, since the micromirror size is congruent with the requirements of a DNA microarray, a simple 1× system can be used. This system has the advantage of simplicity, low aberration and large field of view The projection optics 44 may be of standard design, since the images to be formed are relatively large and well away from the diffraction limit. The lenses 45 and 46 focus the light in the beam 41 passed through the adjustable iris 47 onto the active surface of the substrate. The projection optics 44 and the beam splitter 32 are arranged so that the light deflected by the micromirror array away from the main optical axis (the central axis of the projection optics 44 to which the beams 41 are parallel), illustrated by the beams labeled 40 (e.g., 10 degrees off axis) fall outside the entrance pupil of the projection optics 44 (typically 0.5/5=0.1; 10 degrees corresponds to an aperture of 0.17, substantially greater than 0.1). The iris 47 is used to control the effective numerical aperture (NA) and to ensure that unwanted light (particularly the off-axis beams 40) are not transmitted to the substrate. Resolution of dimensions as small as 0.5 microns are obtainable with such optics systems. Such resolution may separate adjacent mirrors of the micromirrors 36. For manufacturing applications, the micromirror array 35 may be located at the object focal plane of a lithographic I-line lens optimized for 365 nm. Such lenses typically operate with a numerical aperture (NA) of 0.4 to 0.5, and have a large field capability.

The micromirror array device 35 may be formed with a single line of micromirrors (e.g., with 2,000 mirror elements in one line) which is stepped in a scanning system. In this manner the height of the image is fixed by the length of the line of the micromirror array but the width of the image that may be projected onto the substrate 12 is essentially unlimited. By moving the flow cell 18 which carries the substrate 12, the mirrors can be cycled at each indexed position of the substrate to define the image pattern at each new line that is imaged onto the substrate active surface.

Various approaches may be utilized in the fabrication of the DNA probes 16 on the substrate 12, and are adaptations of microlithographic techniques. In a "direct photofabrication approach," the glass substrate 12 is coated with a layer of a chemical capable of binding the nucleotide bases. Light is applied by the projection system 11, deprotecting the OH groups on the substrate and making them available for binding to the bases. After development, the appropriate nucleotide base is flowed into the flow cell and onto the active surface of the substrate and binds to the selected sites using normal phosphoramidite DNA synthesis chemistry. The process is then repeated, binding another base to a different set of locations. The process is simple, and if a combinatorial approach is used, the number of permutations increases exponentially. The resolution limit is presented by the linear response of the deprotection mechanism. Because of the limitations in resolution achievable with this method, methods based on photoresist technology may be used instead, as described, e.g., in McGall, et al., supra. In the indirect photofabrication approach, compatible chemistries exist with a two-layer resist system, where a first layer of, e.g., polyimide acts as a protection for the underlying chemistry, while the top imaging resist is an epoxy-based system. The imaging step is common to both processes, with the main requirement being that the wavelength of light used in the imaging process be long enough not to excite transitions (chemical changes) in the nucleotide bases (which are particularly sensitive at 280 nm). Hence, wavelengths longer than 300 nm should be used. 365 nm is the I-line of mercury, which is the one used most commonly in wafer lithography.

Another form of the array synthesizer apparatus 10 is shown in a simplified schematic view in FIG. 2. In this arrangement, the beam splitter 32 is not used, and the light source 25, optional filter 26, and condenser system 28 are mounted at an angle to the main optical axis (e.g., at 20 degrees to the axis) to project the beam of light 30 onto the array of micromirrors 36 at an angle. In this preferred orientation of the light source 25, the micromirrors 36 are oriented to reflect the light 30 into off axis beams 40 in a first position of the mirrors and into beams 41 along the main axis in a second position of each mirror. In other respects, the array synthesizer of FIG. 2 is the same as that of FIG. 1.

Figure 3:
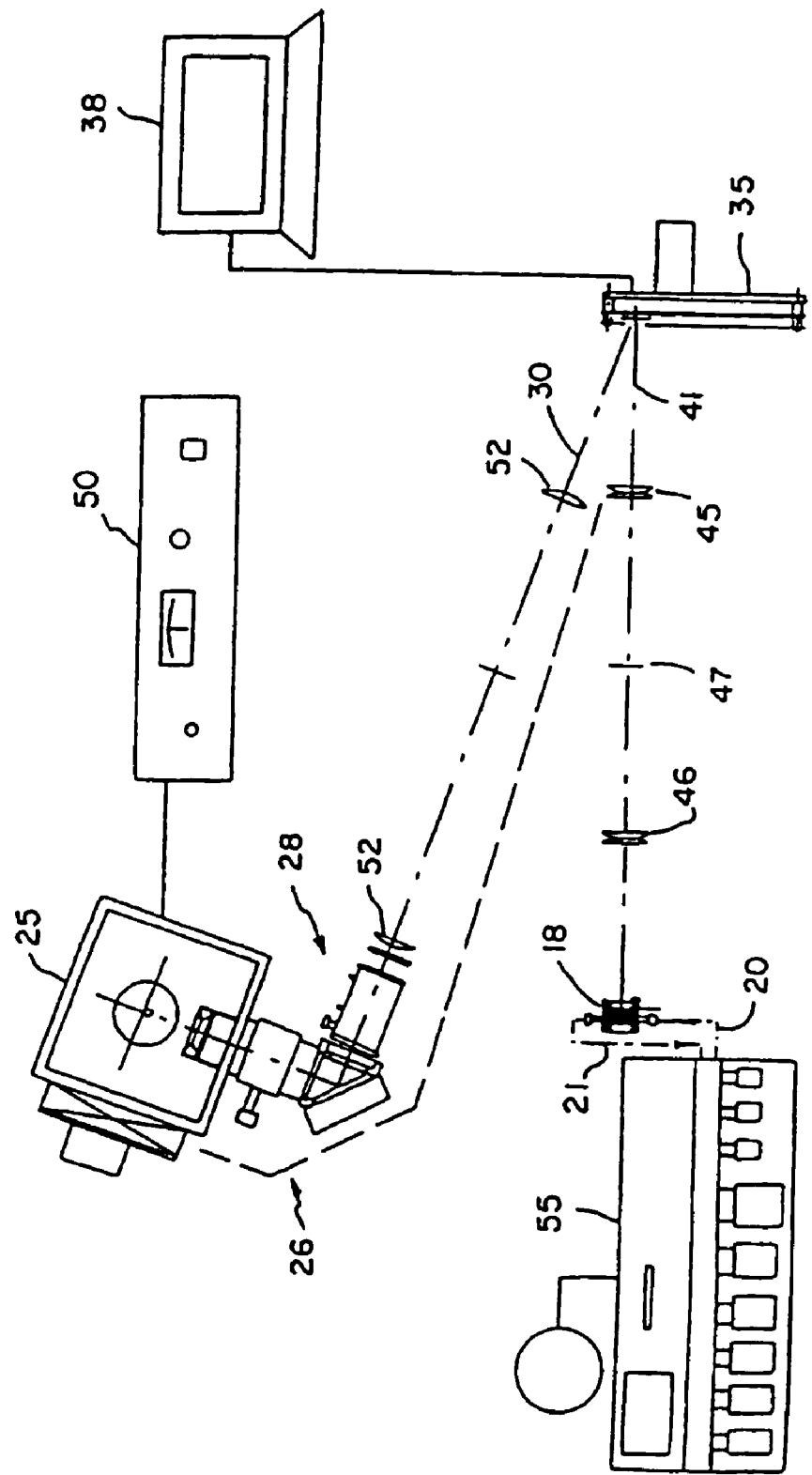
FIG. 3 is a more detailed schematic view of a general telecentric array synthesizer apparatus in accordance with the invention.
Figure 4:
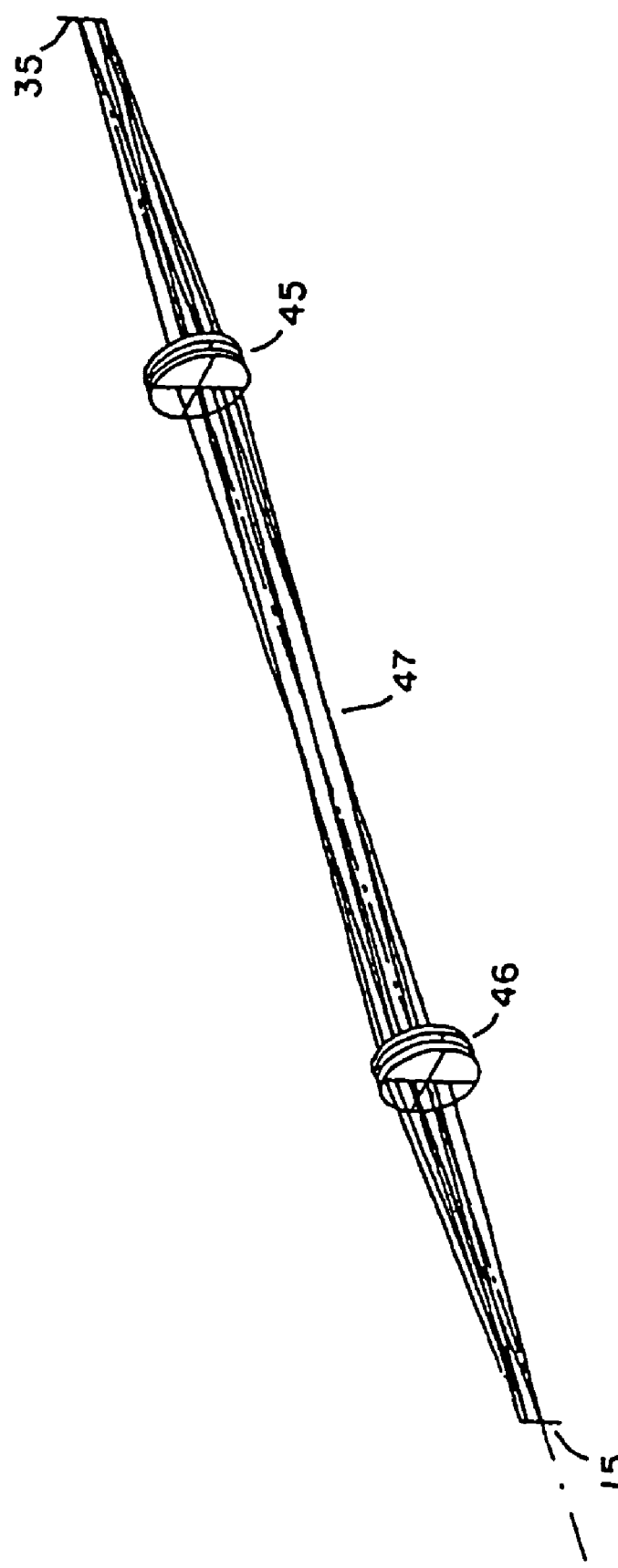
FIG. 4 is an illustrative ray diagram for the refractive optics of the apparatus of FIG. 3.

A more detailed view of a array synthesizer apparatus which uses the preferred off-axis projection arrangement of FIG. 2 is shown in FIG. 3. In a simple implementation of the apparatus of FIG. 3, the source 25 (e.g., 1,000 W Hg arc lamp, Oriel 6287, 66021), provided with power from a power supply 50 (e.g., Oriel 68820), is used as the light source which contains the desired ultraviolet wavelengths. The filter system 26 is composed, for example, of a dichroic mirror (e.g., Oriel 66226) that is used to absorb infrared light and to selectively reflect light of wavelengths ranging from 280 to 400 nm. A water-cooled liquid filter (e.g., Oriel 6127) filled with deionized water is used to absorb any remaining infrared. A colored glass filter (Oriel 59810) or an interference filter (Oriel 56531) may be used to select the 365 nm line of the Hg lamp 25 with a 50% bandwidth of either 50 nm or 10 nm, respectively. An F/1 two element fused silica condenser (Oriel 66024) may be used as the condenser system 28, and with two piano-convex lenses 52 (Melles Griot 01LQP033 and Melles Griot 01LQP023), forms a Kohler illumination system. This illumination system produces a roughly collimated uniform beam 30 of 365 nm light with a diameter just large enough to encompass the 16 mm×12 mm active area of the micromirror array device 35. This beam 30 is incident onto the device 35 at an angle of 20 degrees measured from the normal to the face of the device. It will be clear to one of ordinary skill in the art that many other illumination systems are possible. The micromirror array device 35 is located approximately 700 mm away from the last filter. When the micromirrors are in a first position, the light in the beam 30 is deflected downwardly and out of the system. For example, in this micromirror device the mirrors in their first position may be at an angle of −10 degrees with respect to the normal to the plane of the micromirrors to reflect the light well away from the optical axis. When a micromirror is controlled to be deflected in a second position, e.g., at an angle of +10 degrees with respect to the normal to the plane of the micromirrors, the light reflected from such micromirrors in the second position emerges perpendicularly to the plane of the micromirror array in the beam 41.

Figure 5:
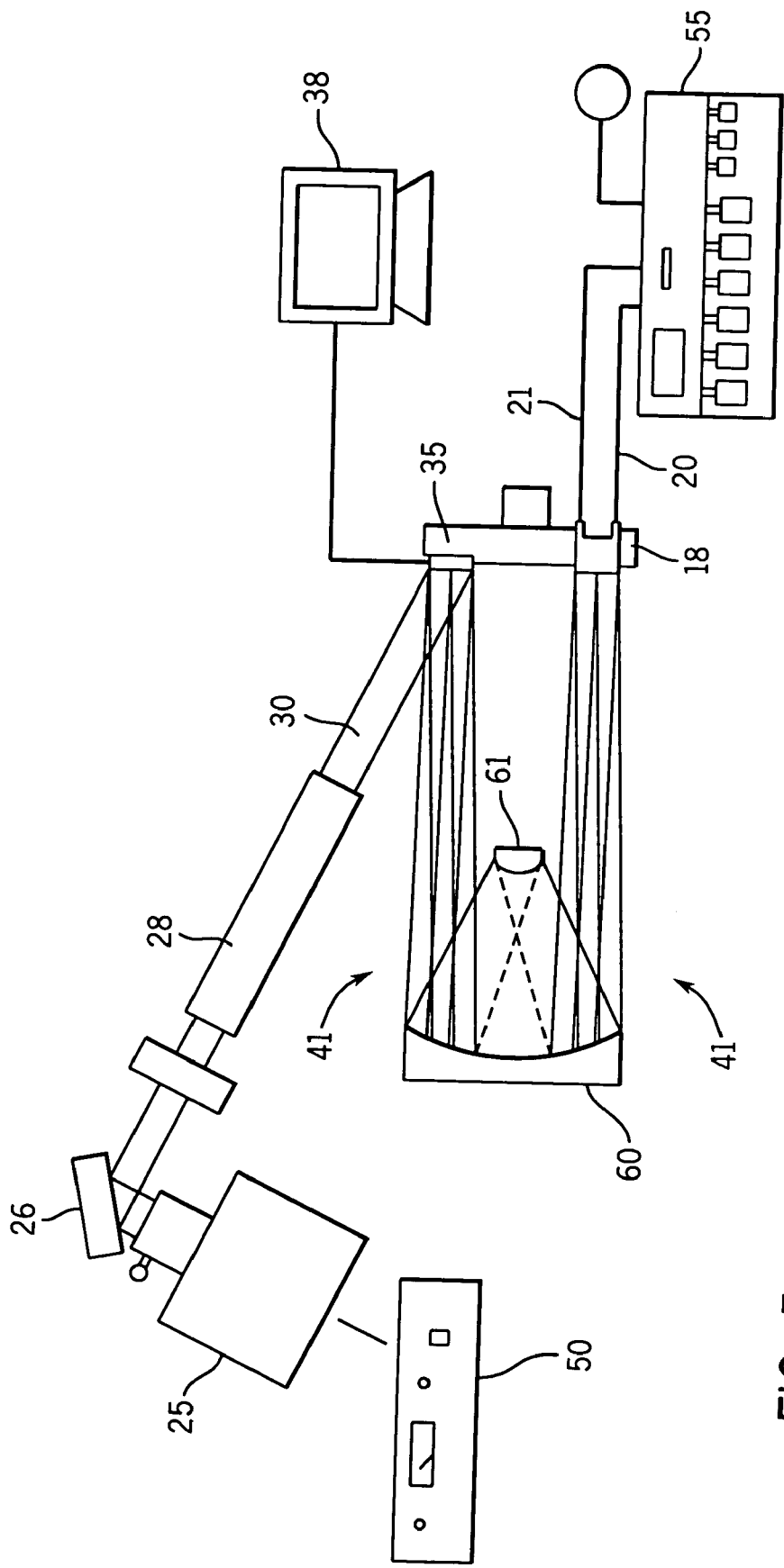
FIG. 5 is a schematic view of a further embodiment of an array synthesizer apparatus in accordance with the invention in which telecentric reflective optics are utilized.

In a preferred embodiment of the array synthesizer apparatus using reflective optics is shown in FIG. 5. Importantly, the reflective optics reduce scatter associated with lenses providing a higher contrast image. In particular, it should be noted that diffusing elements of any kind, including diffusion lenses are not placed down stream of the optical micromirror array device 35 such as would interfere with the contrast of the image. In fact lenses of any kind which may induce scatter are avoided in this critical image region.

An exemplary system utilizes a 1,000 W Hg arc lamp 25 as a light source (e.g., Oriel 6287, 66021), with a filter system formed of a dichroic mirror (e.g., Oriel 66228) that absorbs infrared light and selectively reflects light of wavelengths ranging from 350 to 450 nm. An F/1 two element fused silica condenser lens (Oriel 66024) is used to produce a roughly collimated beam of light 30 containing the 365 nm line but excluding undesirable wavelengths around and below 300 nm. A Kohler illumination system may optionally also be used in the apparatus of FIG. 5 to increase uniformity and intensity. The beam 30 is incident onto the micromirror array device 35 which has an active area of micromirrors of about 16 mm×12 min and which is located about 210 nm from the snout of the UV source 25, with the beam 30 striking the planar face of the micromirror device 35 at an angle of 20 degrees with respect to a normal to the plane of the array. The light reflected from the micromirrors in a first position of the micromirrors, e.g., −10 degrees with respect to the plane of the array, is directed out of the system, whereas light from micromirrors that are in a second position, e.g., +10 degrees with respect to the plane of the array, is directed in the beam 41 toward a reflective telecentric imaging system composed of a concave mirror 60 and a convex mirror 61. Both mirrors are preferably spherical and have enhanced UV coating for high reflectivity although aspherical shapes are possible as well. After executing reflections from the mirrors 60 and 61, the beam 41 is imaged onto the active surface of a glass substrate enclosed in the flow cell 18. In this case the flow cell 18 is co-planar with the micromirrors to complete a Offner optical system The convex mirror defines the aperture of the system. Since the pupil is also located at the convex mirror surface, the system is telecentric. The telecentricity prevents spatial distortion of the image with slight focal distance variations for example when the micromirrors and flow cell 18 are not perfectly co-planar. The beam 41 first strikes the concave mirror, then the convex mirror, and then the concave mirror again to direct it to the flow cell 18. For the system shown, the concave mirror 60 may have a diameter of 152.4 mm, and a spherical mirror surface radius of 304.8 mm (ES F43561), and the convex mirror may have a diameter of 25 mm, and a spherical mirror surface radius of 152.94 mm (ES F45625). Ideally, the radius of curvature of the concave mirror is close to twice that of the convex mirror. Such reflective optical systems are well known and conventionally used in optical lithography in "MicroAlign" type systems. See, e.g., A. Offner, "New Concepts in Projection Mask Aligners," *Optical Engineering*, Vol. 14, pp. 130–132 (1975), and R. T. Kerth, et al., "Excimer Laser Projection Lithography on a Full-Field Scanning Projection System," *IEEE Electron Device Letters*, Vol. EDL-7(5), pp. 299–301 (1986).

Figure 6:
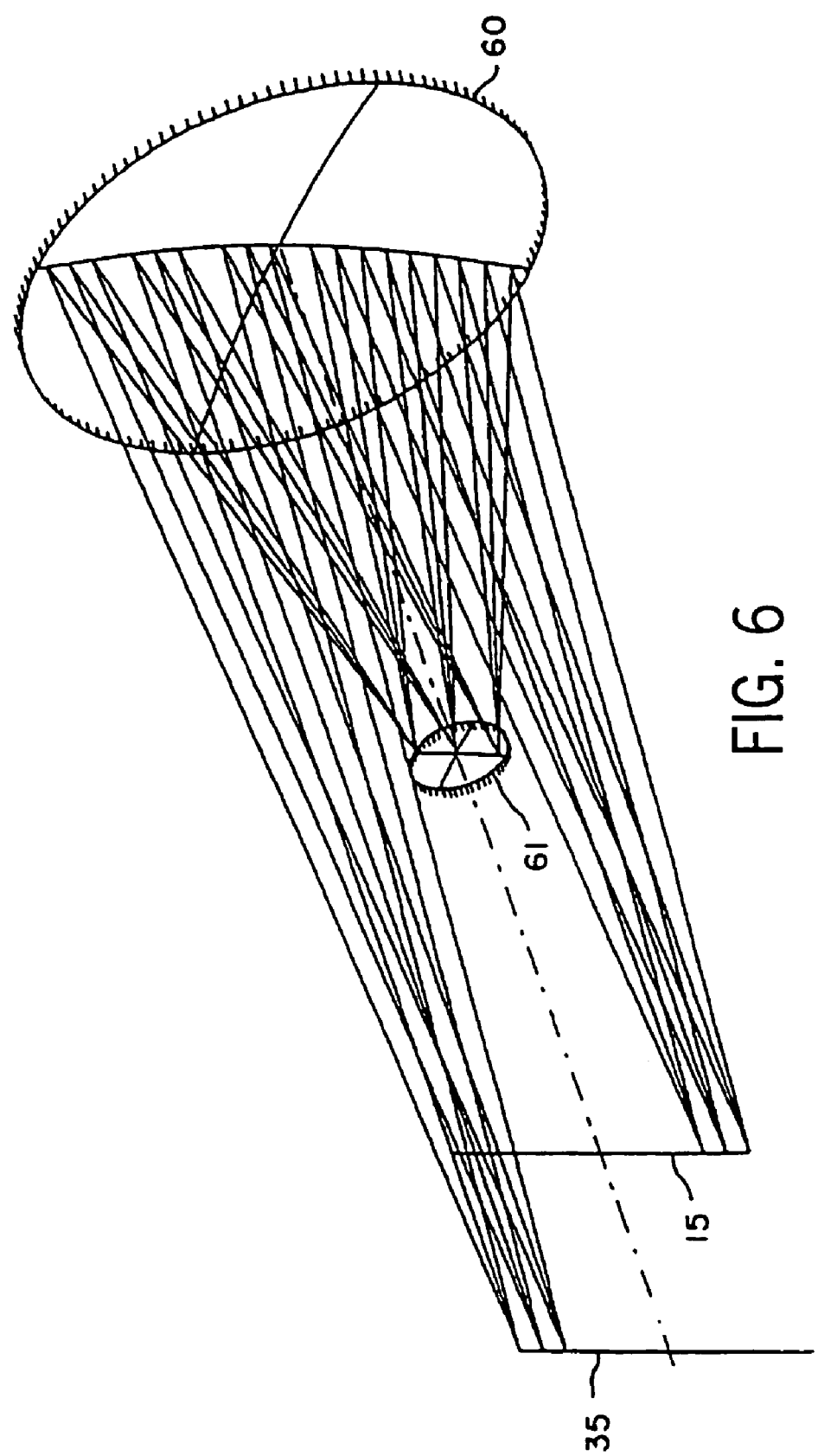
FIG. 6 is an illustrative ray diagram for the reflective optics of the apparatus of FIG. 5.
Figure 7:
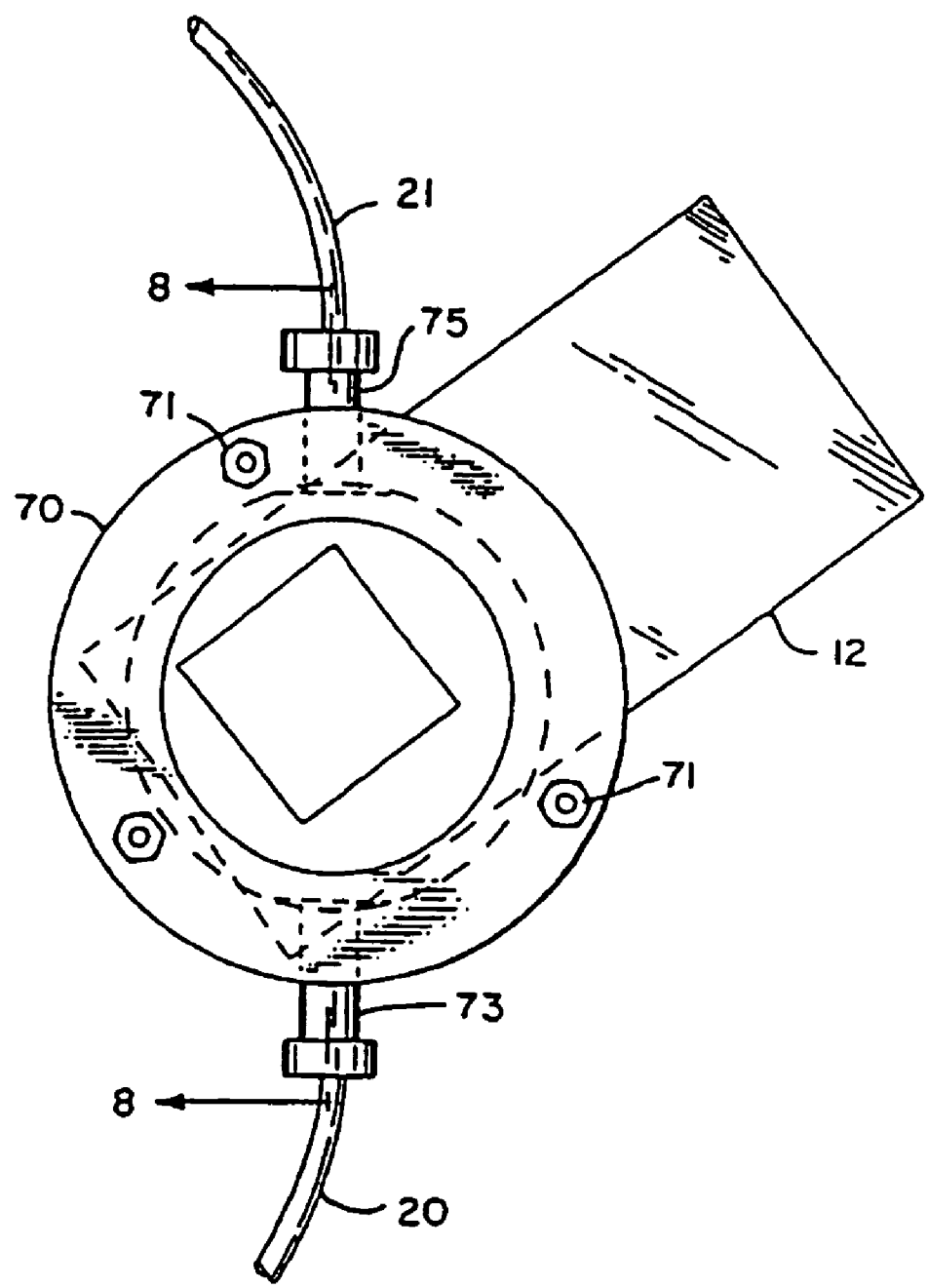
FIG. 7 is a top plan view of a reaction chamber flow cell which may be utilized in the array synthesizer apparatus of the invention to form an array of probes directly on a substrate.

FIG. 6 illustrates image formation for the preferred optical system of FIG. 5. Fans of rays originating in the center of the object (the micromirror array device), at the edge, and at an intermediate position are shown in FIG. 6. The rays reflect first from the concave mirror 60, then from the convex mirror 61, then from the concave mirror 60 again, to form an inverted image of the face of the micromirror array device.

The refractive or reflective optical systems are both designed to minimize aberrations such as coma and spherical aberration via cancellation. Both of the telecentric optical systems of FIGS. 3 and 5 are 1:1 imaging systems. A reflective system has the potential advantages of eliminating chromatic aberration allowing alignment of the system using visible light, as well as being compact and less expensive.

Another preferred system for doing 1:1 imaging would be a Wynne-Dyson type system which combines concave mirror with lenses and prisms. See, e.g., F. N. Goodall, et al., "Excimer Laser Photolithography with 1:1 Wynne-Dyson Optics," Optical/Laser Microlithography, SPIE Vol. 922 (1988); and B. Ruff, et al., "Broadband Deep-UV High NA Photolithography System," Optical/Laser Microlithography II, SPIE Vol. 1088 (1989).

Figure 8:
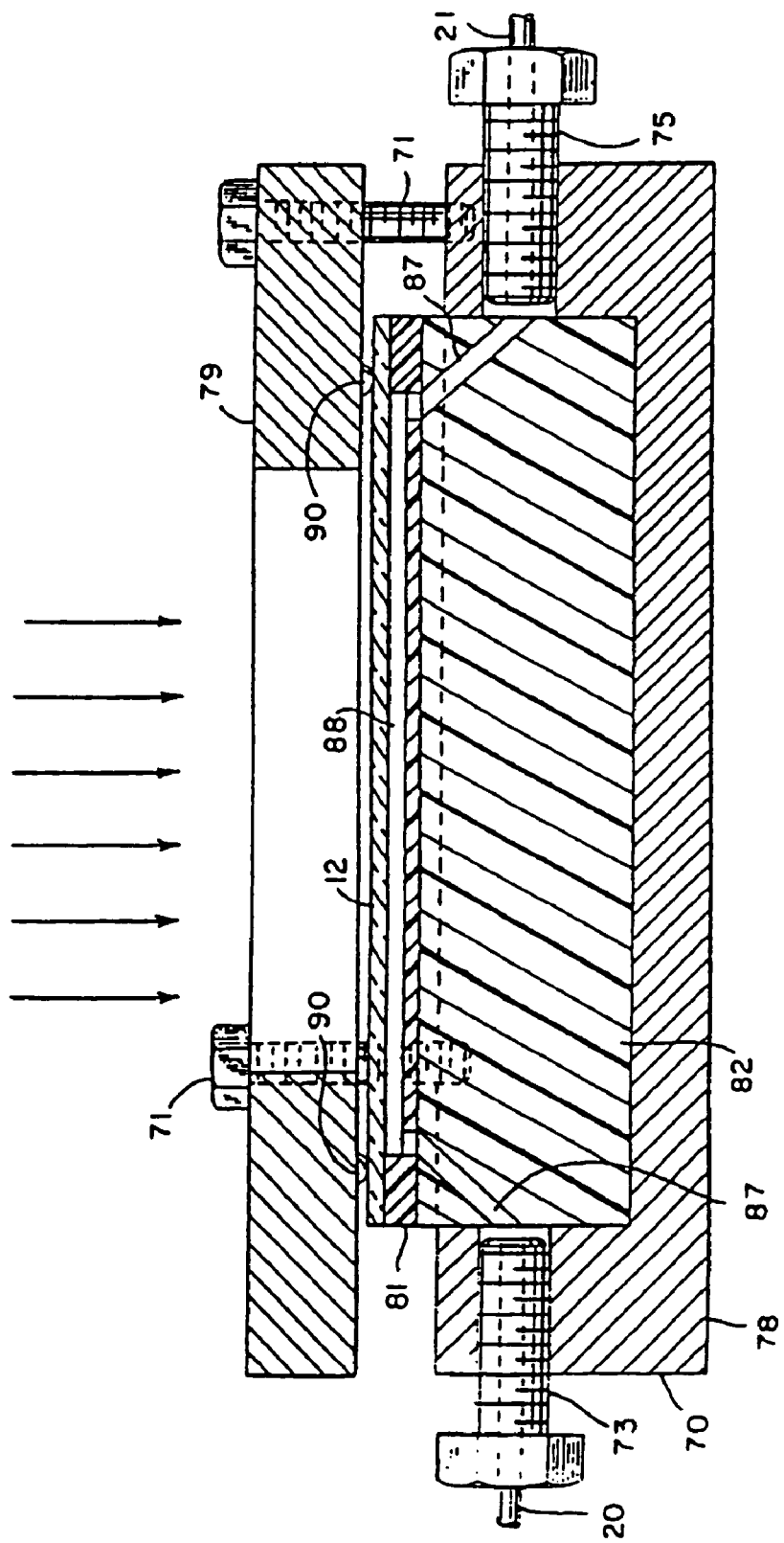
FIG. 8 is a cross-sectional view through the reaction chamber flow cell of FIG. 7 taken generally along the lines 8—8 of FIG. 7.

More detailed views of different flow cells which may be utilized with the apparatus of the invention to form an array of probes is shown in FIGS. 7–8, and FIGS. 15–16. The exemplary flow cell 18 in FIGS. 7 and 8 may be used to synthesize probes directly on a substrate and includes an aluminum housing 70, held together by bolts 71, having an inlet 73 connected to an input port line 20 and an outlet 75 connected to an output port line 21. As illustrated in the cross-sectional view of FIG. 8, the housing 70 includes a lower base 78 and an upper cover section 79 which are secured together over the substrate with the bolts 71. The substrate 12, e.g., a transparent glass slide, is held between the upper plate 79 and a cylindrical gasket 81 (e.g., formed of Kal RezJ), which in turn is supported on a nonreactive base block 82 (e.g., TeflonJ), with an inlet channel 85 extending from the inlet 73 to a sealed reaction chamber 88 formed between the substrate 12 and the base block 82 that is sealed by the gasket, and with an outlet channel 89 extending from the reaction chamber 88 to the outlet 75. The bolts 71 can be screwed and unscrewed to detachably secure the substrate 12 between the cover section and the base to allow the substrate to be replaced with minimal displacement of the base of the flow cell. Preferably, as shown in FIG. 8, a rubber gasket 90 is mounted at the bottom of the plate 79 to engage against the substrate at a peripheral region to apply pressure to the substrate against the gasket 81. If desired, the flow cell may also be used as a hybridization chamber during readout.

Figure 9:
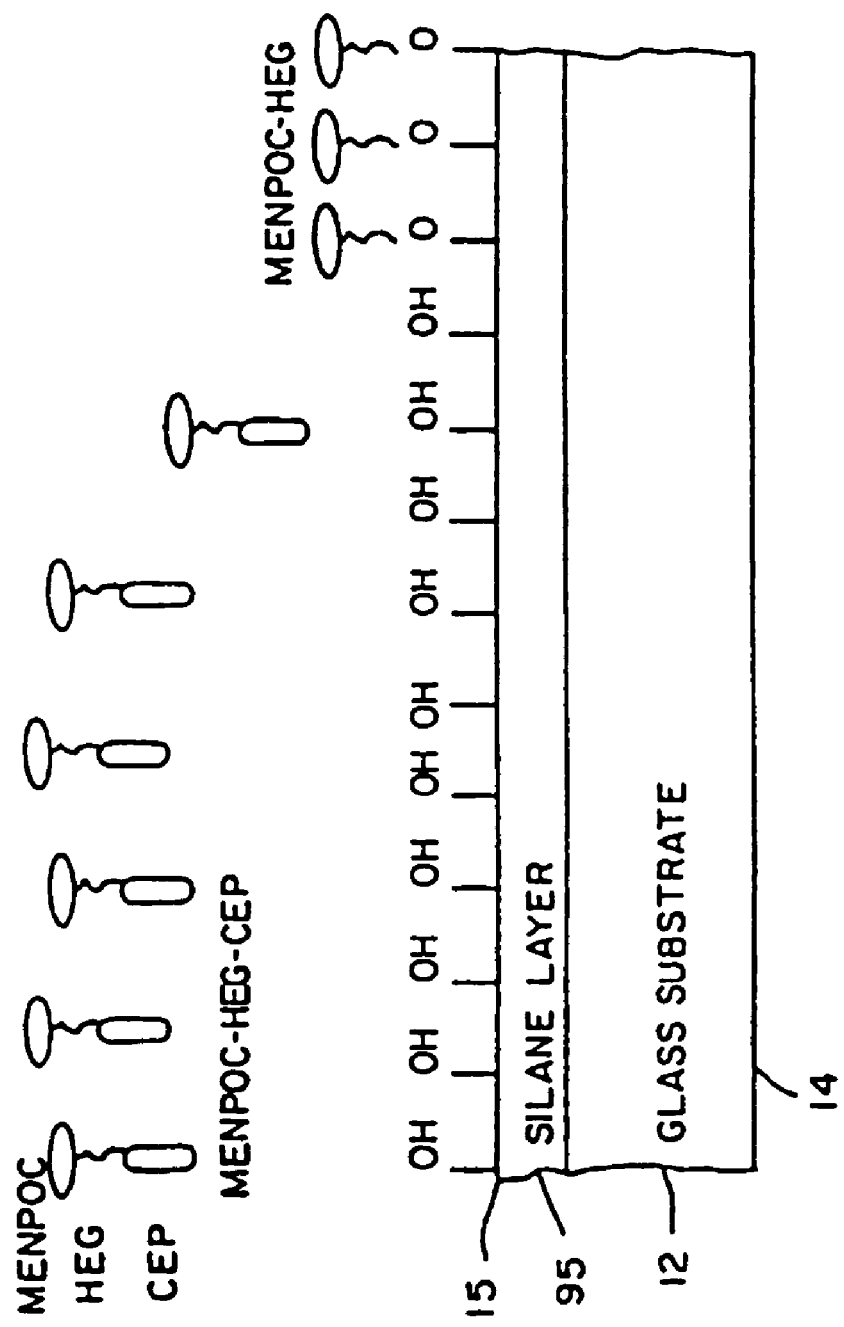
FIG. 9 is an illustrative view showing the coating of a substrate with a photolabile linker molecule.

An exemplary process for forming DNA probes directly on a substrate is illustrated with respect to the schematic diagrams of FIGS. 9–14. FIG. 9 illustrates the coating of the substrate 12, having a silane layer 95 forming the active surface 15 thereof, with the photolabile linker molecule MENPOC-HEG coated on the silane layer using standard phosphoramidite chemistry. MENPOC-HEG-CEP=18-O-[(R,S)-(1-(3,4-(Methylenedioxy)-6-nitrophenyl)ethoxy)carbonyl]-3,6,9,12,15,18-hexaoxaoctadec-1-yl O⁻-2-cyanoethyl-N, N-Diisopropylphosphoramidite. The silane layer was made from N (3-(triethoxysilyl)-propyl)-4-hydroxybutyramide. At the step shown in FIG. 9, the substrate can be exposed to light and active free OH groups will be exposed in areas that have been exposed to light.

Figure 10:
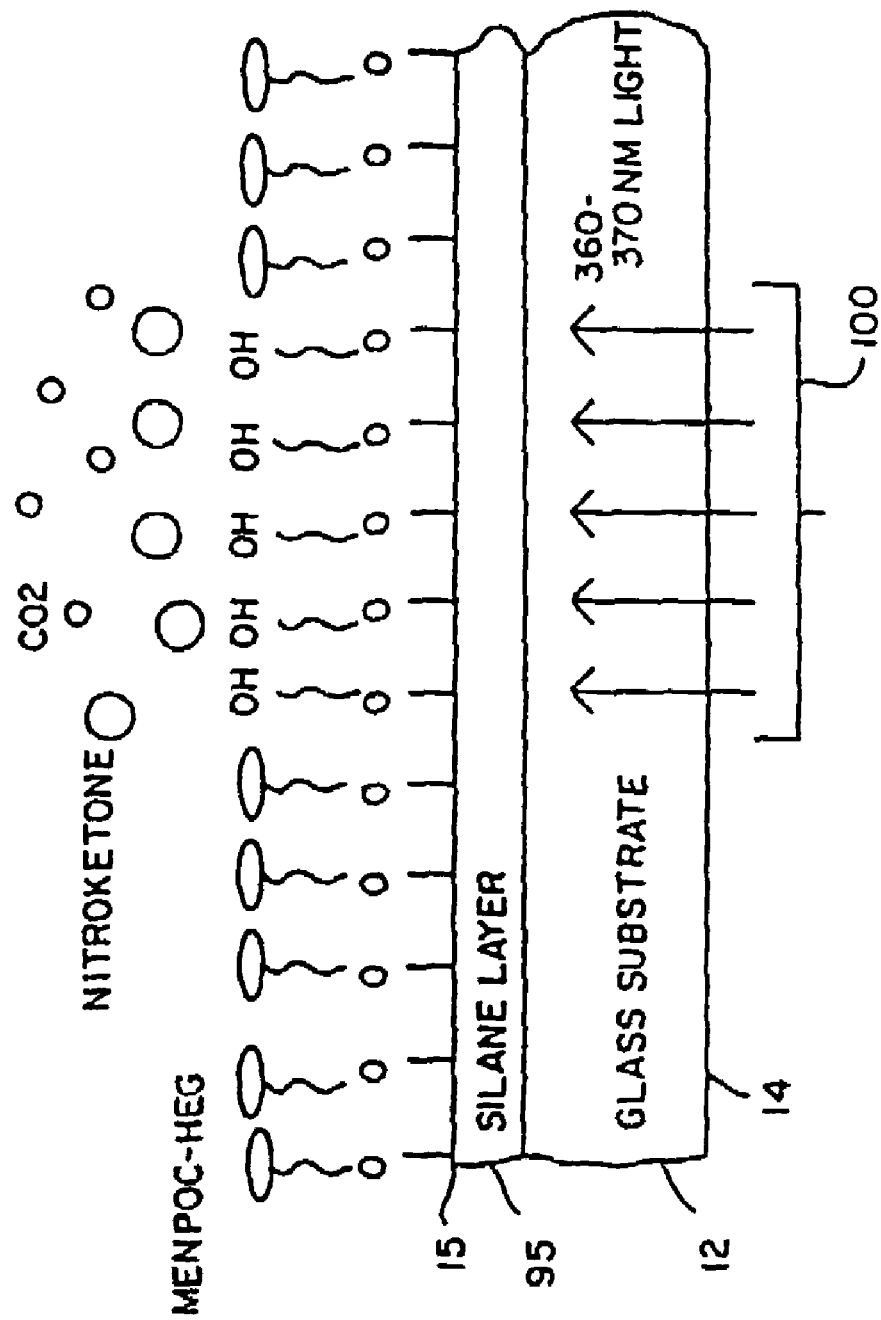
FIG. 10 is an illustrative view showing the photo-deprotection of the linker molecule and the production of free OH groups on a substrate.
Figure 11:
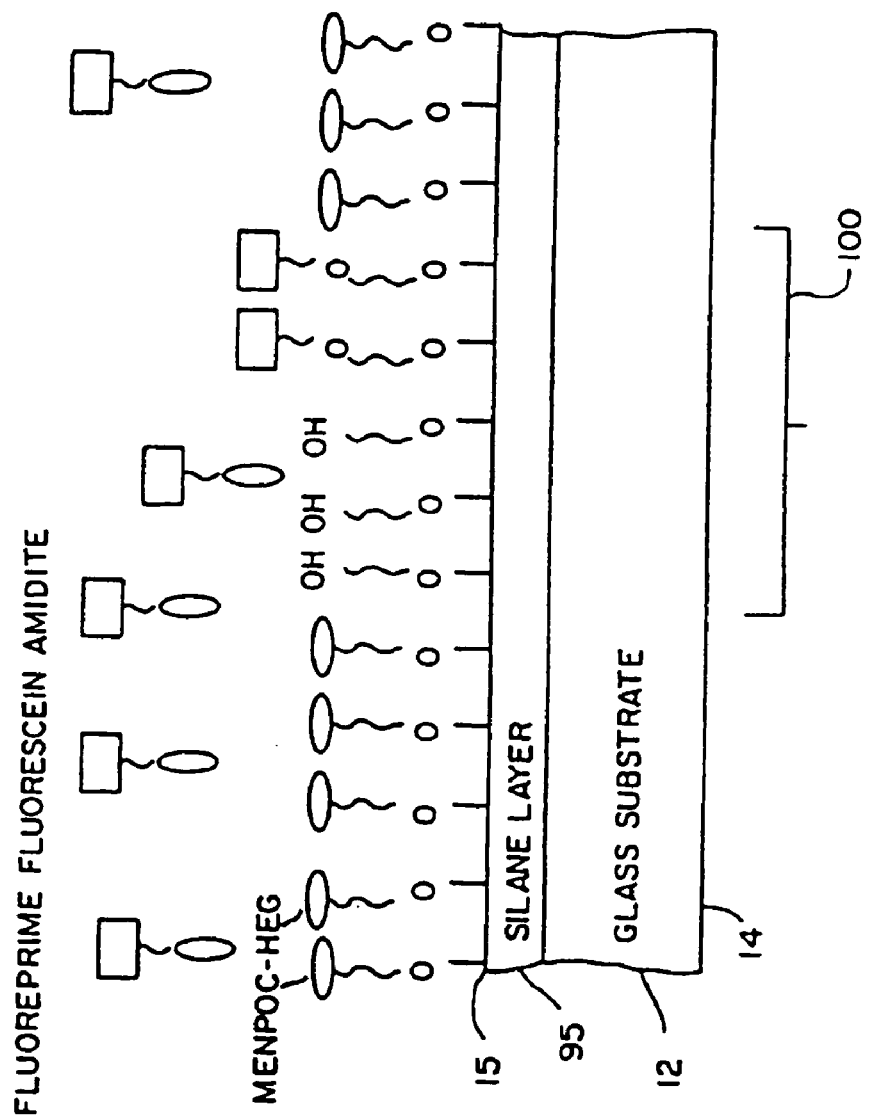
FIG. 11 is an illustrative view showing the coupling of markers to free OH groups produced by the photo-deprotection of the linker molecules on a substrate.
Figure 12:
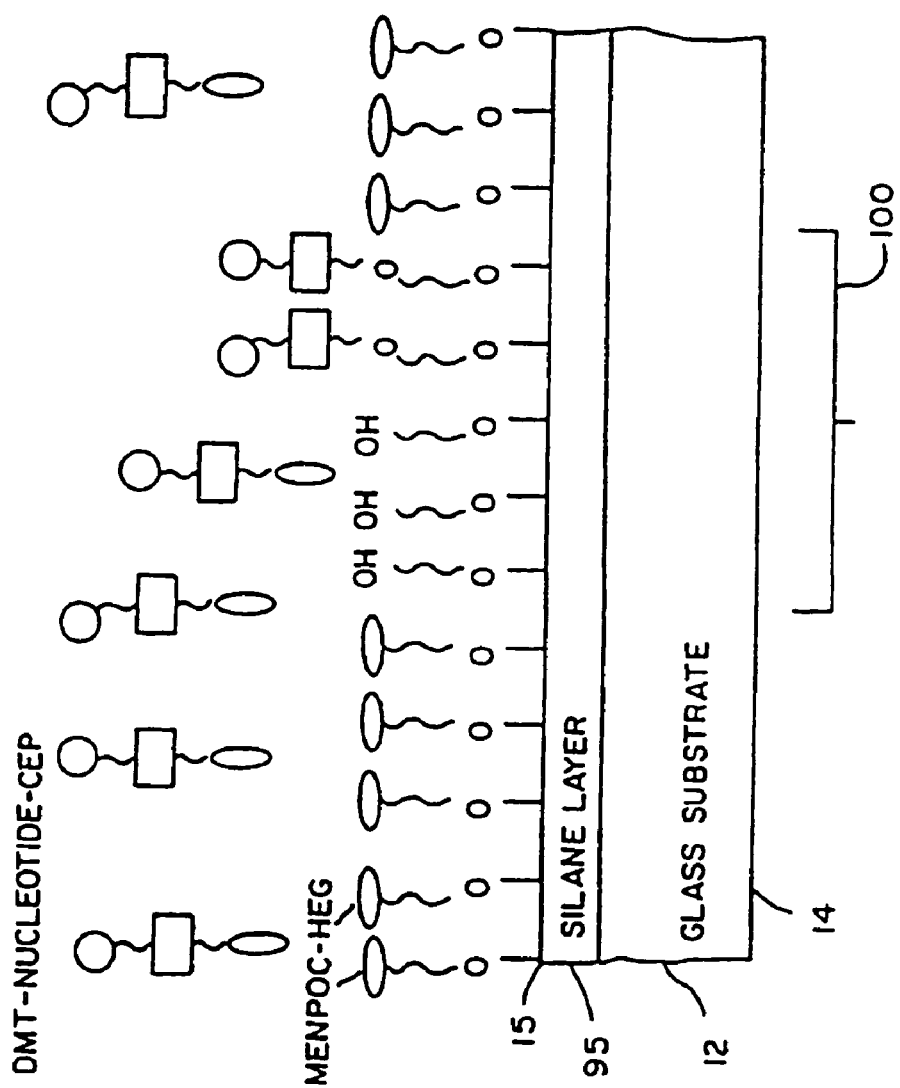
FIG. 12 is an illustrative view showing the coupling of DMT-nucleotide to free OH groups produced from photo-deprotection of the linker molecules on a substrate.
Figure 13:
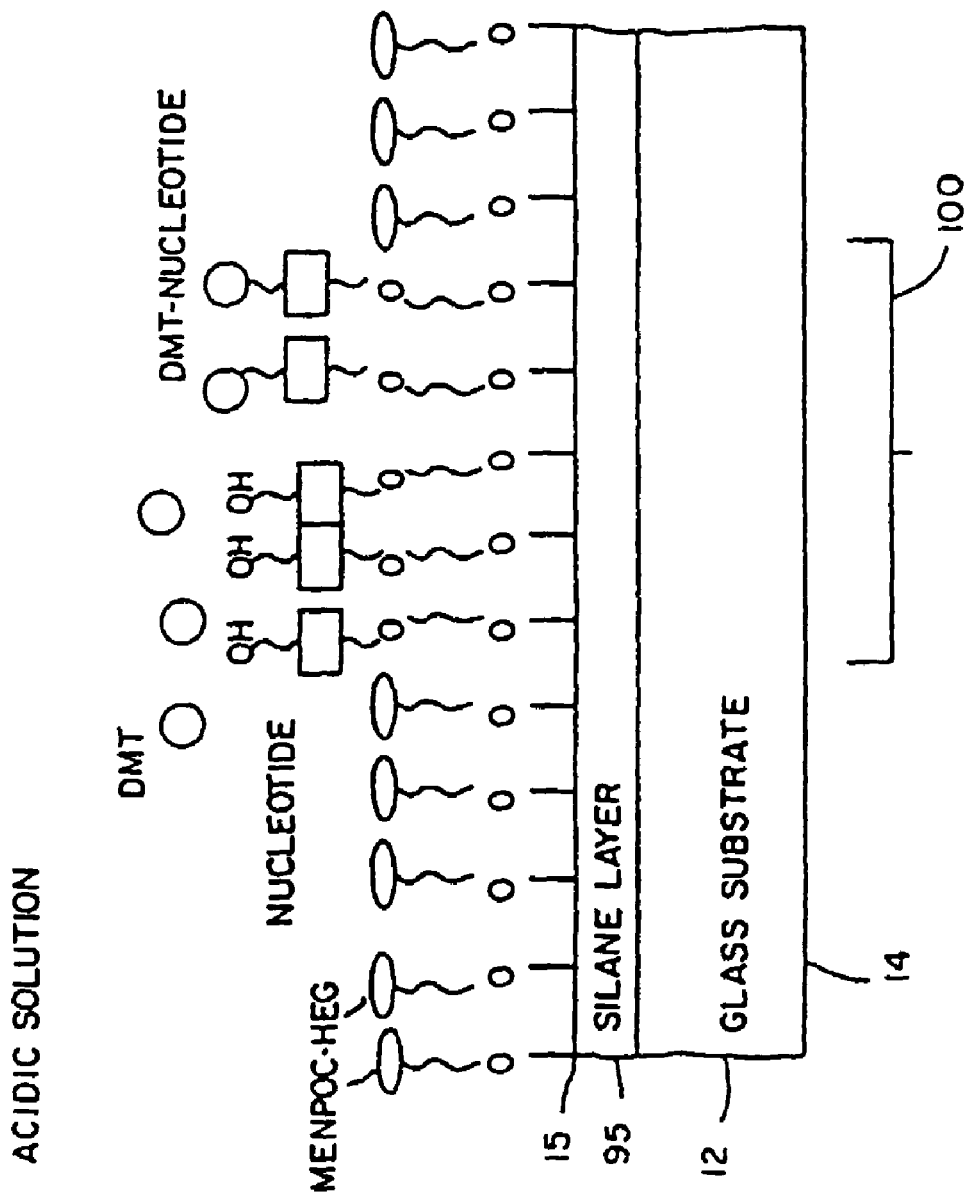
FIG. 13 is an illustrative view showing acid deprotection of DMT nucleotides on a substrate.
Figure 14:
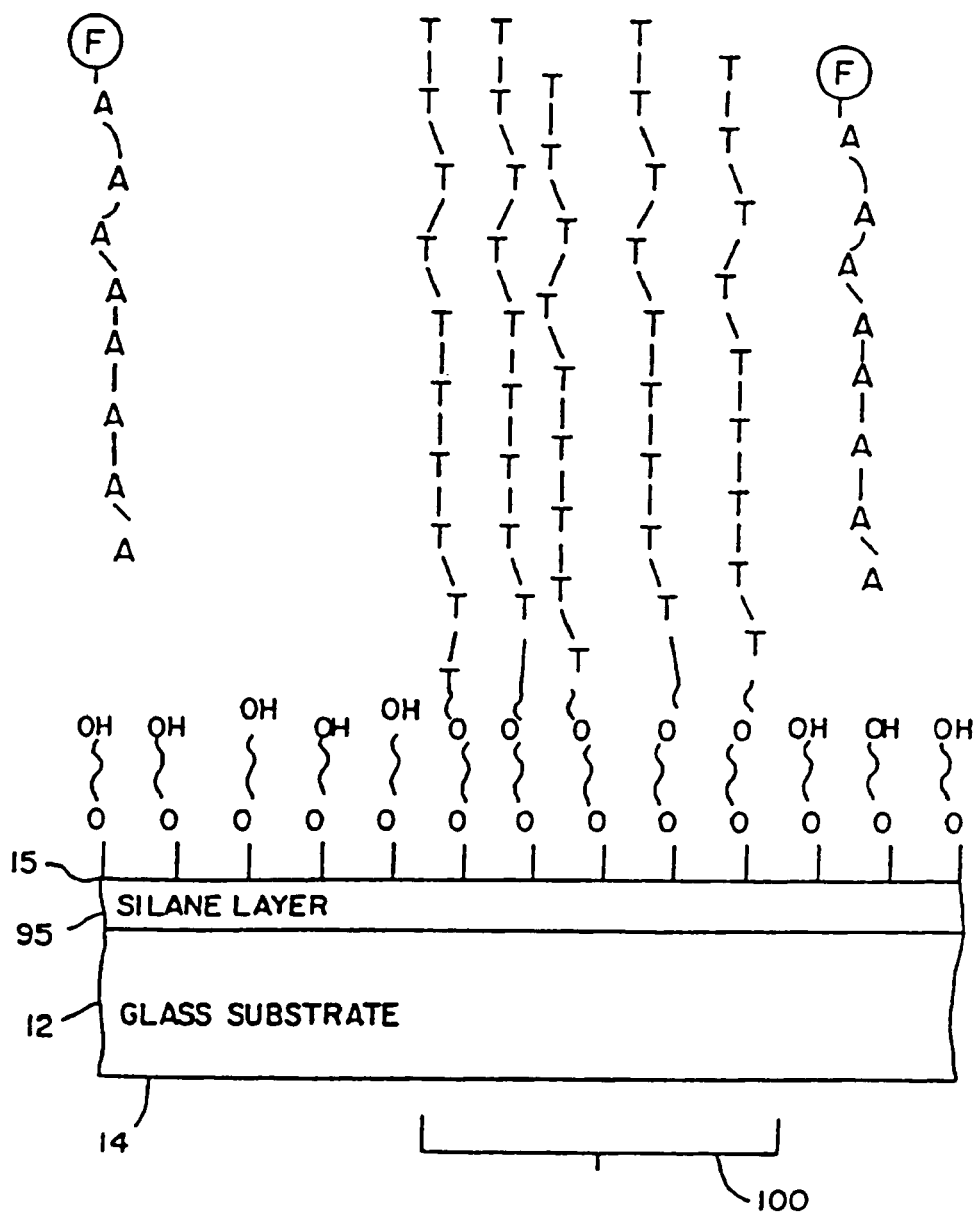
FIG. 14 is an illustrative view showing the hybridization of poly-A probes labeled with fluorescein to poly-T oligonucleotides on a substrate and synthesized from DMT nucleotide-CEPs.
Figure 15A:
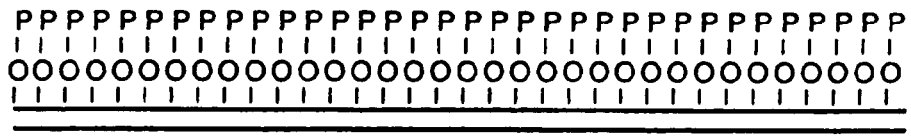
FIG. 15 are illustrative views similar to those of FIGS. 9–14 showing an alternative embodiment in which the synthesis of DNA probe sequence is carried out using small DNA polymers rather than single nucleotides.
Figure 15B:
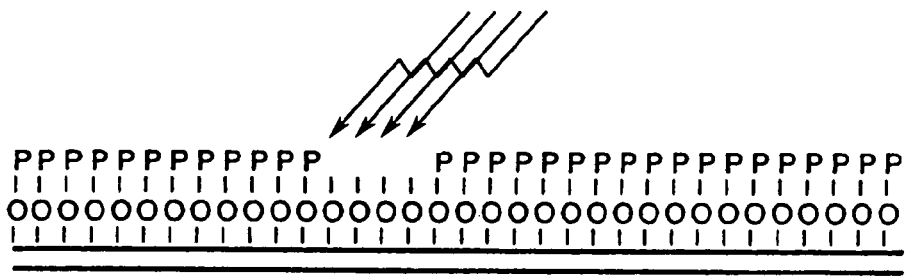
Figure 15C:
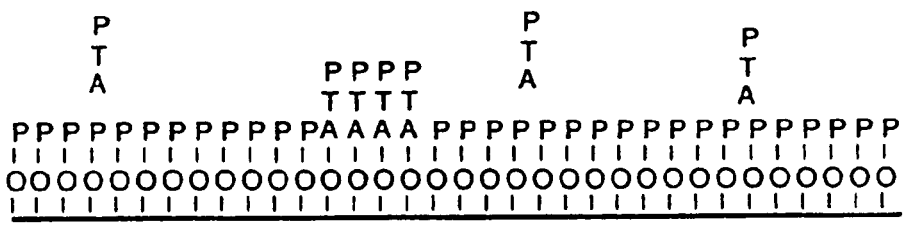
Figure 15D:
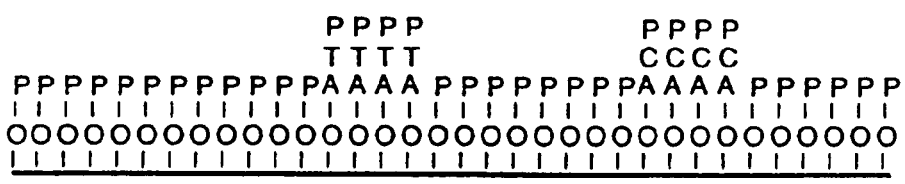
Figure 15E:
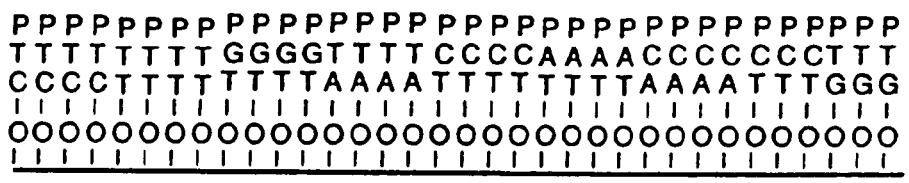

FIG. 10 illustrates the photo-deprotection of the MENPOC-HEG linker and the production of free OH groups in the area 100 that is exposed to light. FIG. 11 illustrates the coupling of FluorePrimeJ fluorescein amidite to free OH groups produced from photo-deprotection of MENPOC-HEG. FIG. 12 illustrates the coupling of DMT-nucleotide to free OH groups produced from photo-deprotection of MENPOC-HEG linker. FIG. 13 illustrates the step of acid deprotection of DMT-nucleotides in the area 100 exposed to light. FIG. 14 illustrates the hybridization of poly-A probe labeled with fluorescein with poly-T oligonucleotides synthesized from DMT-nucleotide-CEPs.

Synthesis of Probes from DNA Polymers

An alternative embodiment for making an array is illustrated in FIG. 15. In FIG. 15A, the entire surface of the substrate on which the array is to be made is covered with photolabile protecting group ("P") by a liner ("O"). While any suitable photolabile protective groups can be used, the preferred chemistry uses 5'-[1-nitrophenyl)-propyloxycarbonyl]-2'-deoxynucleoside phosoramides (NPPOC), as described in Hasan et al., *Tetrahdron*, 53:12, pp. 4247–4264 (1997) and Beier and Hoheisel, *Nucl. Acids Res.* 2000, 28:4 (2000). As an alternative, the substrate can also be covered with a single nucleotide, or identical short polynucleotides, again with a photolabile protective group at their termini. The micromirror array is then illuminated to degrade the NPPOC in selected array segment or cell where DNA is to be added. This is illustrated in FIG. 15B. Then DNA dimers, in this case dimers of sequence AT, are exposed to the substrate, thereby chemically bonding to the array only in the cell to which the light had been directed by the micromirror array. This is illustrated in FIG. 15C. The small DNA polymers include another photolabile protective group appended to their terminus. Then this same process of light illumination and dimer addition is repeated for the dimer sequence AC, as shown in FIG. 15D. This same process is then repeated 14 more times for each of the other possible DNA dimers that can be made from combinations of two nucleotides. At the end of the completion of a layer of the DNA probe synthesis process, as illustrated in FIG. 15E, two nucleotides have been added to each nascent probe in the microarray. This process is then restarted in the next level, and the process is repeated until the probes are built out to a desired length.

Projection Optics with Relaxed Resolution

Figure 16:
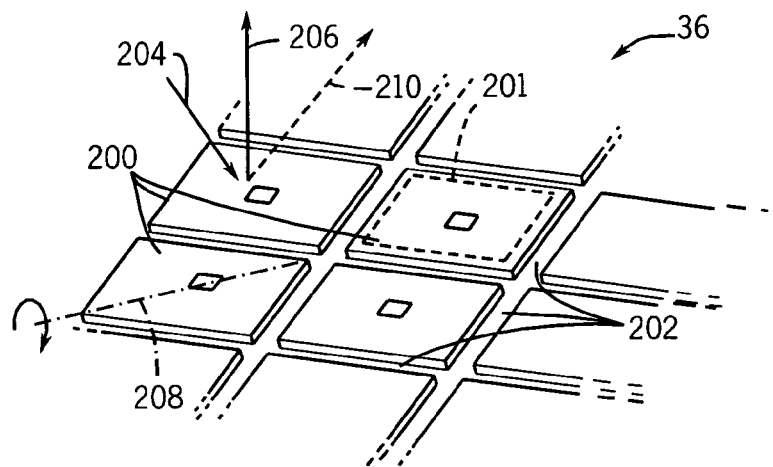
FIG. 16 is a perspective view of the surface of the micromirror array showing the pixels defined by the mirrors and the separating lanes.

Referring now to FIG. 16, the surface of the micromirrors 36 presents a rectilinear grid of square mirrors 200 having a generally square outline of sixteen micrometers. Each mirror 200 defines a single pixel 201 shown by a dotted line.

Separating the mirrors 200 from each other are lanes 202 providing a gap between adjacent edges of mirrors 200. The lanes 202, in commercial micromirrors 36, are one micrometer in width and thus define a pitch separating the mirrors 200 of seventeen micrometers.

When a given mirror 200 is in the on state, incident light 204 at 20 degrees from a normal to the surface of the micromirrors 36 is reflected off the mirrors 200 as a beam 206 parallel to the normal. Each of the mirrors 200 may tip about a deflection axis 208 diagonal across its area from the projection or "on" state and (deflecting the light into the pupil) to an absorption or "off" state in which the incident light 204 is deflected out of the pupil along a beam 210 at approximately 10° from the normal to the surface of the micromirrors 36 to an absorber. When a given mirror 200 is in the on state, an image of the mirror 200 will produce a brightly illuminated pixel 201. When a given mirror 200 is in the absorption state, the image of the mirror 200 will produce a dark pixel 201 caused by a deflection of the light to an absorber rather than to the projection optics as described above.

Figure 17:
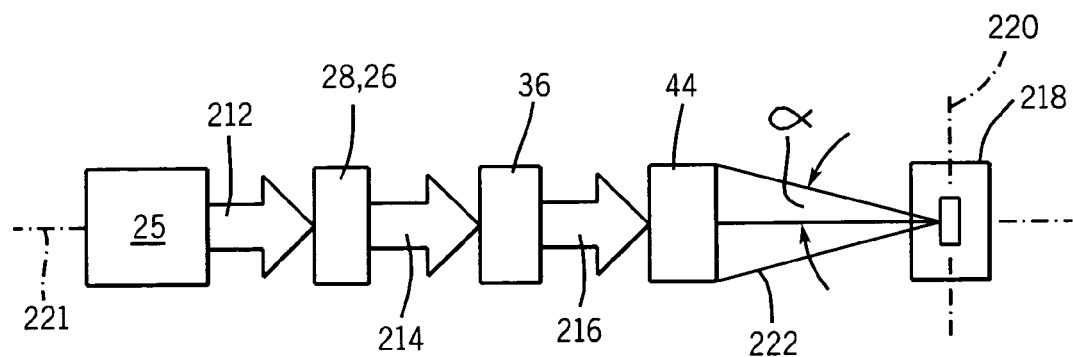
FIG. 17 is a block diagram generalizing the optical systems described above for providing an image on the reactor, and illustrating computation of the half angle defining the numerical aperture of the projection optics.

Referring now to FIG. 17, a generalized optical system preferably implemented per FIG. 5 described above, includes a light source 25 producing an uncollimated light beam 212 received by a condenser system 28 and 26 to produce collimated and filtered light to 214. This collimated and filtered light 214 is modulated by the mirror array 36 (the object of the optical system) to produce modulated light 216. Projection optics 44 focus the modulated light 216 onto a reactor 218 being any of the various reaction systems described. The components of this optical system of FIG. 17 are arranged along a optical path 221 being generally understood not to be constrained to a line but following the path of light as may be changed by reflection or refraction. As has been described above, more generally the components of the optical system may be refractive and reflective elements, however, the projection optics are preferably reflective in design with fewer surfaces than refractive optics, so as to reduce scatter occurring at each surface of the optical elements.

The reactor 218 where the synthesis of DNA probes occurs is located at the object's conjugate plane and embraces a focal plane 220 positioned at the apex of cone of illumination 222. The cone of illumination 222 is defined by the exit aperture of the final element of the projection optics 44 (generally the element diameter) and the focal length of the projection optics 44. This is independent of whether the projection optics are refractive or reflective or a combination of both. A half angle α is one half of the angle of the apex of cone of illumination 222 and defines the numerical aperture (NA) of the system according to the formula:

$$NA = \sin(\alpha).$$

Since for small angles $\sin(\alpha)$ may be approximated by $\alpha$, the numeric aperture may be approximated by the illuminated aperture of the final element of the projection optics (the objective) divided by twice its focal length. In the implementation of FIG. 5 the aperture of the objective is controlled by the diameter of the convex lens.

Figure 18:
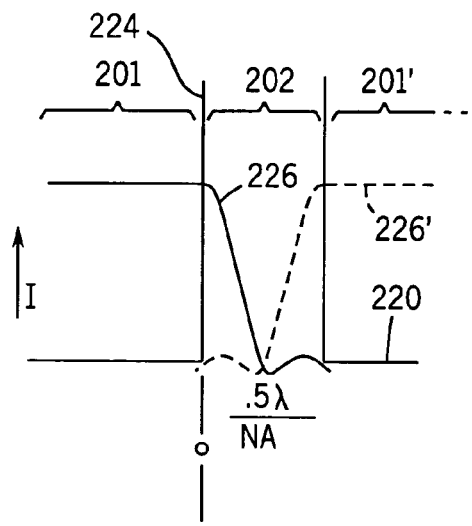
FIG. 18 is a simplified plot of light intensity taken in proximity to the lanes of FIG. 18 at a focal plane illustrating the calculation of numerical aperture necessary for resolving the lanes under a first resolution criteria.

Referring now to FIG. 18, the fall off of light at an interface 224 between a pixel 201 and a pixel 201' within a lane 202 and at the focal plane 220 will be dependent upon the numerical aperture of the projection optics 44 and the wave length λ of the light among other factors. In image formation theory (see for Principles of Optics: Electromagnetic Theory of Propagation, Interference and Diffraction of Light by Max Born, Emil Wolf) the optical system acts as a low-pass frequency filter. The object illuminance I(x,y) is analyzed as a Fourier integral I'($f_x$, $f_y$) where the spatial frequencies $f_x$, $f_y$ extend from $-\pi/\lambda$ to $\pi/\lambda$. The optical system allows only the spatial frequencies in the range of $-NA\pi/\lambda$ to $NA\pi/\lambda$ to be transmitted. When the image is formed at the object's conjugate plane, high spatial frequencies are missing resulting in a broadened image of the original object. Generally, the light associated with a given pixel 201 will spread in a diffraction pattern 226 into the image of the lane 202 that may, for example, reach a minimum within the lane 202 when the lane 202 is fully resolved. That location of that minimum from the edge of the pixel 201 is a measure of the resolution of the projection optics and will approximately equal $$\frac{0.5\lambda}{NA}$$

following standard lithographic language. More generally the resolution of the projection optics may be defined as its ability to image a line, termed the line width (LW) and defined by the equation:

$$LW = \frac{k\lambda}{NA}$$

where λ is the wavelength of light, NA is the numerical aperture of the projection optics 44, and k is an image quality factor no less than 0.5 for coherent light and typically somewhere between 0.7 and 0.5. In special cases, k can be lower than 0.5 (e.g., with phase masks).

For the light of the diffraction patterns 226 and 226' (the latter shown by dotted line) from two adjacent pixels 201 and 201' to be completely suppressed at some point within the one micrometer wide lane 202, at wavelength of 365 nanometers, the resolution of the projection optics 44 must have a numerical aperture of 0.365 or larger.

Nevertheless, as will now be described, in the present invention, far lower numerical apertures are acceptable and even desirable though they produce line widths values much exceeding 0.5 micrometers, and in one preferred embodiment, produce a line width as large as 2.7 micrometers, far in excess of the lane width. Such line widths may be associated with numerical apertures as low as 0.08, more than four times lower than that which might be intuitively required.

Figure 19:
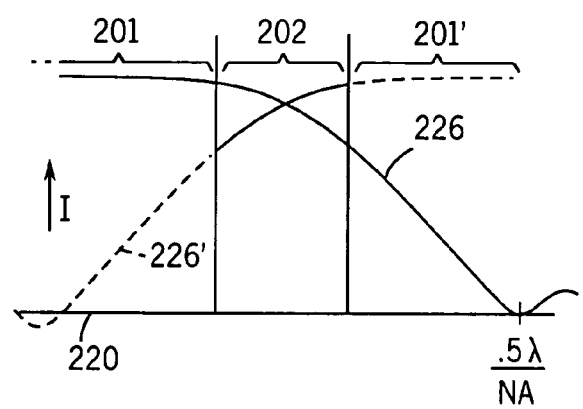
FIG. 19 is a figure similar to that of FIG. 18 showing relaxed resolution requirements of the present invention which allow overlapping illumination of the lanes between pixels inadequate to resolve the lanes.

As illustrated in FIG. 19, the minimum of the diffraction pattern 226 for the pixel 201 with smaller numerical apertures produced by the present invention will extends into adjacent pixel 201' and the minimum of the diffraction pattern 226' for the pixel 201 with smaller numerical apertures produced by the present invention will extends into adjacent pixel 201. In this case, the lane 202 will receive an overlap of light spilling over from pixels 201 and 201'.

Figure 20:
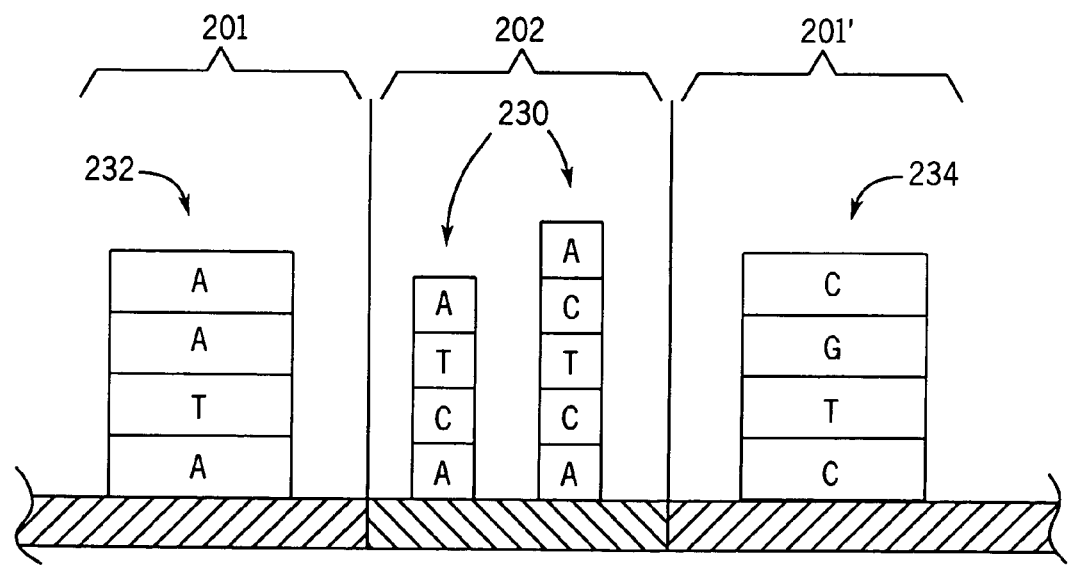
FIG. 20 is a schematic representation of the regions of FIGS. 18 and 19 showing synthesis of the nucleotide sequences for DNA probes within the pixels and showing jumbled probe fragments within the lanes subject to the overlapping illumination from adjacent pixels.

Referring also to FIG. 20, this overlapping of light in the lane 202 will cause the synthesis of DNA fragments 230 subject to both the light used to synthesize DNA fragment 230 for pixel 201 and 234 for pixel 201'. The combined influence of the light used to synthesize a DNA probe 232 at pixel 201 and the light used to synthesize a DNA probe 234 at pixel 201' will result in DNA fragments 230 being a composite of base pairs and sequencing found in both of DNA probe 232 and DNA probe 234, yet DNA fragments 230, by virtue of that combination will match neither DNA probe 232 and DNA probe 234. Further, because of the reduced light intensity in the lane 202, DNA fragments 230 will be subject to increased synthesis errors on a random basis, thus causing a heterogeneity in the fragments 230 formed in the lane 202. Thus, on the off-chance that some of the DNA fragments 230 may provide a sequence that could hybridize with DNA being tested, that fluorescent signal produced by that matching will be minimal.

The invention allows the use of projection optics 44 having insufficient resolution to fully resolve the lanes 202 or even the edges of the pixels 201.

While the lanes as described above are gaps between physical mirrors, it will be understood that larger lanes may be created by using the mirror themselves electrically aimed so as to create dark bands of separation between the pixels. For example, in a cell composed of two rows and two columns of mirrors (four total mirrors) all but one mirror may be set in the off state so as to create a lane approximately one mirror wide about a single mirror that may switch between the projecting and off state. The present invention is equally applicable to this situation and hence the term "lane" as used herein and in the claims should be understood to cover both a gap between mirrors and mirrors themselves when they are fixed in the off state.

It is understood that the particular embodiments set forth herein are illustrative and not intended to confine the invention, but embraces all such modified forms thereof as come within the scope of the following claims.

We claim:
1. An apparatus for constructing DNA probes comprising:
  (a) a reactor providing a reaction site at which nucleotide addition reactions may be conducted;
  (b) a light source providing a light capable of promoting nucleotide addition reactions;
  (c) a set of electronically addressable micromirrors positioned along an optical path between the light source and the reactor to receive and reflect the light; and
  (d) a prismatic and kaleidoscopic light homogenizer positioned on the optical path between the light source and the electronically addressable micromirrors, the prismatic and kaleidoscopic light homogenizer having a light transmitting refractive prism followed by an internally reflecting kaleidoscope element, the latter positioned to received light refracted by the refractive prism.

2. The apparatus of claim 1 wherein the refractive prism is a pyramid having a regular polygonal base, wherein the base is positioned substantially perpendicular to the optical path.

3. The apparatus of claim 2 wherein the base is a octagon.

4. The apparatus of claim 1 wherein the kaleidoscope element is a tube having a polygonal cross section at least two adjacent sides of which are internally reflective.

5. The apparatus of claim 4 wherein all sides of the kaleidoscope element are internally reflective and the cross section is a regular polygon of a class that may be tiled over a plane.

6. The apparatus of claim 1 including further:
   (e) a lens-free optical system using mirrors to conduct light from the electronically addressable micromirrors to the reactor.

7. The apparatus of claim 1 including:
   (e) projection optics positioned along the optical path between the reaction site and the electronically addressable micromirrors to focus an image at the reaction site, the projection optics selected to substantially minimize scatter and diffusion of the image.

8. An apparatus for catalyzing a reaction on a substrate comprising:
   a light source;
   a micromirror positioned to redirect light from said light source toward said substrate;
   a prismatic and kaleidoscopic homogenizer positioned between said light source and said micromirror and having a light transmitting refractive prism followed by an internally reflecting kaleidoscope element positioned to received light refracted by the refractive prism;
   a computer connected to, and controlling, said micromirror, and a reaction chamber is placed in the path of light redirected by said micromirror, wherein light that is redirected by said micromirror catalyzes a chemical reaction proximate said substrate in said reaction chamber.

9. The apparatus of claim 8 including further:
   a lens-free optical system using mirrors to conduct light from the micromirrors to the substrate.

10. The apparatus of claim 8 further including:
   projection optics positioned micromirror and the substrate to focus an image at the substrate, the projection optics selected to substantially minimize the introduction of scatter and diffusion of the image between the micromirror and the substrate.

* * * * *